United States Patent

Cohen et al.

[11] Patent Number: 4,785,017

[45] Date of Patent: Nov. 15, 1988

[54] 3,4-DIHYDRO-2H-1-BENZOPYRAN DERIVATIVES

[75] Inventors: Noal Cohen, Montclair; Giuseppe F. Weber, Cedar Grove, both of N.J.

[73] Assignee: Hoffmann-La Roche Inc., Nutley, N.J.

[21] Appl. No.: 614,368

[22] Filed: May 29, 1984

Related U.S. Application Data

[63] Continuation-in-part of Ser. No. 507,383, Jun. 24, 1983, abandoned.

[51] Int. Cl.[4] .................. C07D 311/60; A61K 31/35
[52] U.S. Cl. .................... 514/456; 549/407; 549/405
[58] Field of Search ............... 549/405, 407; 514/456

[56] References Cited

U.S. PATENT DOCUMENTS 4,511,685  4/1985  Nissen et al. .................. 549/405

Primary Examiner—Nicky Chan
Attorney, Agent, or Firm—Jon S. Saxe; Bernard S. Leon; Richard J. Mazza

[57] ABSTRACT

The invention relates to compounds of the formula

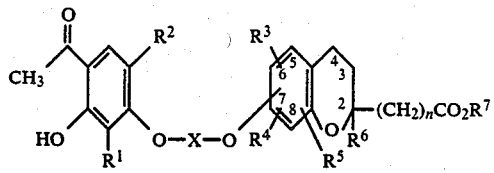

and

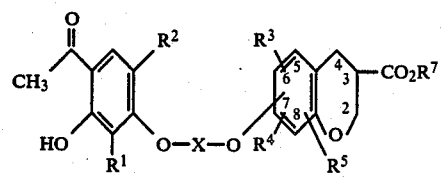

wherein $R^1$ is hydrogen or lower alkyl; $R^2$ is hydrogen or halogen; $R^3$, $R^4$ and $R^5$ are hydrogen, acyl or lower alkyl; $R^6$ and $R^7$, independently, are hydrogen or lower alkyl; X is alkylene$_{3-7}$; and n is an integer of zero to four; provided that only one of $R^3$, $R^4$ or $R^5$ can be acyl;

enantiomers thereof, and, when $R^7$ is hydrogen, salts thereof with pharmaceutically acceptable bases.

The compounds of formulas I and II are useful as agents for the treatment of allergic conditions.

13 Claims, No Drawings

3,4-DIHYDRO-2H-1-BENZOPYRAN DERIVATIVES

RELATED APPLICATIONS

This application is a continuation-in-part of U.S. patent application Ser. No. 507,383, filed June 24, 1983, now abandoned.

DETAILED DESCRIPTION OF THE INVENTION

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl and the like. The term "halogen" denotes all the halogens, that is, bromine, chlorine, fluorine and iodine. The term "acyl" denotes an "alkanoyl" group derived from an aliphatic carboxylic acid of 1 to 7 carbon atoms, for example, formyl, acetyl, propionyl, and the like; and an "aroyl" group derived from an aromatic carboxylic acid, such as benzoyl and the like. The term "alkylene" denotes a straight or branched chain radical of 3 to 7 carbon atoms, for example, propylene, 2-methylpropylene, butylene, pentamethylene, hexamethylene, heptamethylene and the like. The term "aryl" denotes phenyl or phenyl bearing one or more substituents selected from the group consisting of halogen, trifluoromethyl, lower alkyl, lower alkoxy, nitro, amino, lowr alkylamino and di-lower alkylamino. The term "aralkyl" denotes a straight or branched chain lower alkyl group in which one or more of the hydrogen atoms have been replaced by an aryl group, for example, benzyl and the like.

The invention relates to compounds of the formula

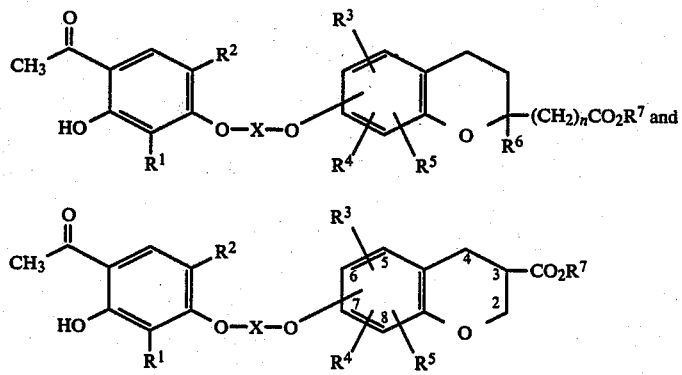

wherein $R^1$ is hydrogen or lower alkyl; $R^2$ is hydrogen or halogen; $R^3$, $R^4$ and $R^5$ are hydrogen, acyl or lower alkyl; $R^6$ and $R^7$, independently, are hydrogen or lower alkyl; X is alkylene$_{3-7}$; and n is an integer of zero to four; provided that only one of $R^3$, $R^4$ or $R^5$ can be acyl;
enantiomers thereof, and, when $R^7$ is hydrogen, salts thereof with pharmaceutically acceptable bases.

A preferred group of compounds of the invention are those represented by the formula

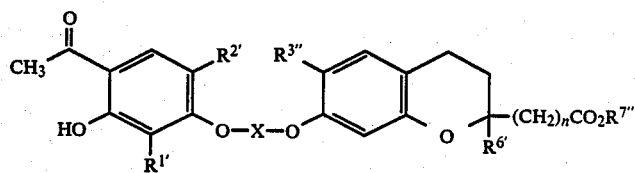

wherein $R^{1'}$ is lower alkyl, $R^{2'}$ is hydrogen, $R^{3''}$ is acyl, $R^{6'}$ is hydrogen and $R^{7''}$ is hydrogen.

A more preferred group of compounds of the invention are those of formula I in which $R^1$ is lower alkyl; $R^2$ is hydrogen; $R^3$ is acyl; $R^4$, $R^5$, $R^6$ and $R^7$ are hydrogen; X is alkylene of 3 to 5 carbon atoms.

A still more preferred group of compounds of the invention are those of formula I in which $R^1$ is propyl, $R^2$ is hydrogen, $R^3$ is acetyl; $R^4$, $R^5$, $R^6$ and $R^7$ are hydrogen; X is alkylene of 3 to 5 carbon atoms.

Preferred compounds of formulas I and II are:
racemic-6-acetyl-7-[5-(4-acetyl-3-hydroxy-2-propylphenoxy)pentyloxy]-3,4-dihydro-2H-1-benzopyran-2-carboxylic acid;
(S)-(+)-6-acetyl-7-[5-(4-acetyl-3-hydroxy-2-propylphenoxy)pentyloxy]-3,4-dihydro-2H-1-benzopyran-2-carboxylic acid;
racemic-6-acetyl-7-[3-(4-acetyl-3-hydroxy-2-propylphenoxy)propoxy]-2-methyl-8-propyl-2H-1-benzopyran-2-propanoic acid; and
racemic-7-[3-(4-acetyl-3-hydroxy-2-propylphenoxy]-3,4-dihydro-2H-1-benzopyran-2-carboxylic acid.

Exemplary of the compounds of formulas I and II are:
(R)-6-acetyl-7-[5-(4-acetyl-3-hydroxy-2-propylphenoxy)pentyloxy]-3,4-dihydro-2H-1-benzopyran-2-carboxylic acid;
(S)-6-acetyl-7-[5-(4-acetyl-3-hydroxy-2-propylphenoxy)pentyloxy]-3,4-dihydro-2H-1-benzopyran-2-carboxylic acid;
racemic-7-[3-(4-acetyl-3-hydroxy-2-propylphenoxy)propoxy]-3,4-dihydro-2H-1-benzopyran-2-butanoic acid;
racemic-8-[3-(4-acetyl-3-hydroxy-2-propylphenoxy)propoxy]-3,4-dihydro-7-acetyl-2H-1-benzopyran-2-carboxylic acid;
racemic-5-acetyl-6-[5-(4-acetyl-3-hydroxy-2-propylphenoxy)pentyloxy]-3,4-dihydro-2H-1-benzopyran-2-propanoic acid;

racemic-6-acetyl-7-[5-(4-acetyl-3-hydroxy-2-propyl-phenoxy)pentyloxy]-3,4-dihydro-2H-1-benzopyran-2-butanoic acid;

racemic-6-propanoyl-7-[7-(4-acetyl-3-hydroxy-2-propylphenoxy)heptyloxy]-3,4-dihydro-8-propyl-2H-1-benzopyran-2-butanoic acid;

(R)-(−)-6-acetyl-7-[5-(4-acetyl-3-hydroxy-2-propyl-phenoxy)pentyloxy]-3,4-dihydro-2H-1-benzopyran-2-carboxylic acid; and the like.

The compounds of formula I of the invention can be prepared as hereinafter described in Reaction Schemes I and II which follow:

Reaction Scheme I

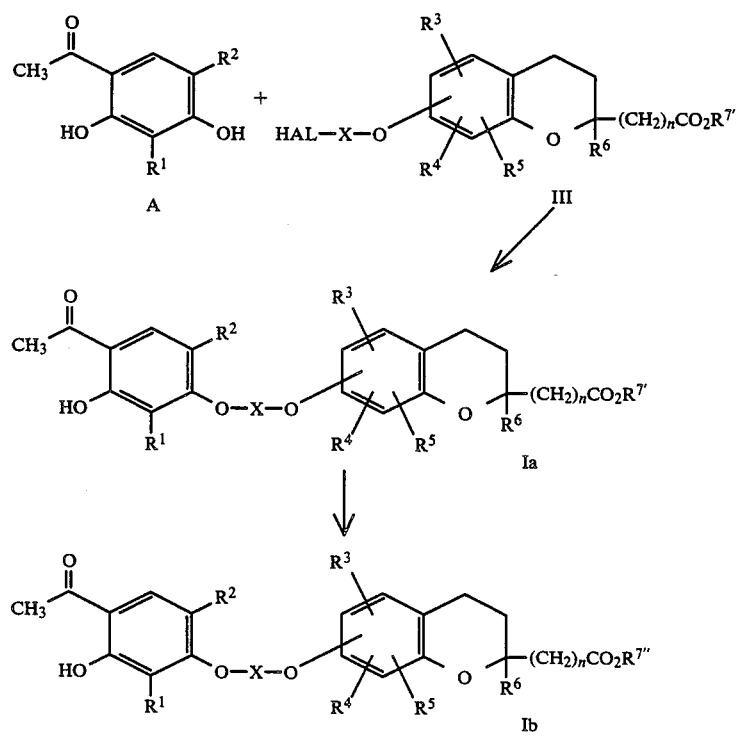

wherein $R^1$, $R^2$, $R^3$, $R^4$, $R^5$, $R^6$, X and n are as previously described, $R^{7'}$ is lower alkyl, $R^{7''}$ is hydrogen and HAL is halogen.

In Reaction Scheme I, the reaction of a compound of formula A, which are known compounds or can be prepared according to known procedures, with a compound of formula III to yield a compound of formula Ia is carried out under anhydrous conditions in an inert solvent, for example, acetone, methylethyl ketone, di- ethyl ketone, dimethylformamide or the like, at the reflux temperature of the reaction mixture, in dimethylformamide, preferably at a temperature in the range of from about 70° to about 100° C., and in the presence of an acid acceptor, for example, potassium carbonate or the like. The preferred solvent is a mixture of acetone and dimethylformamide. The resulting compound of formula Ia can be recovered utilizing conventional methods, for example, crystallization, chromatography or the like.

A compound of formula Ia can be converted to a compound of formula Ib by hydrolysis which is carried out with an alkali metal hydroxide, for example, lithium hydroxide, sodium hydroxide, potassium hydroxide or the like, in a mixture of water and a water miscible solvent, for example, methanol, ethanol, tetrahydrofuran or the like, at a temperature in the range of from about room temperature to the reflux temperature. The resulting compound of formula Ib can be recovered utilizing conventional methods, for example, crystallization, chromatography or the like.

Reaction Scheme II

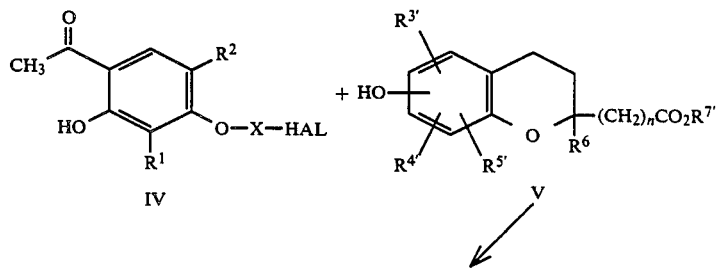

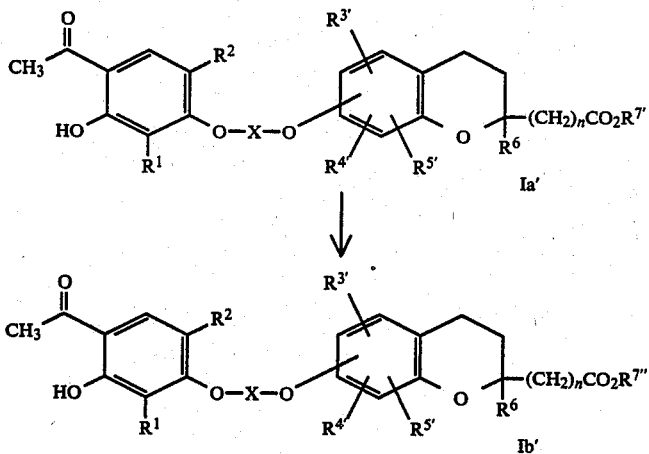

wherein $R^1$, $R^2$, $R^6$, $R^{7'}$, $R^{7''}$, HAL, X and n are as previously described, and $R^{3'}$, $R^{4'}$ and $R^{5'}$ are hydrogen or lower alkyl.

In Reaction Scheme II, the reaction of a compound of formula IV, which are known compounds or can be prepared according to known procedures, with a compound of formula V to yield a compound of formula Ia' is carried out under anhydrous conditions in an inert solvent, for example, acetone, methylethyl ketone, diethyl ketone, dimethylformamide or the like, at the reflux temperature of the reaction mixture, in dimethylformamide, preferably at a temperature in the range of from about 70° to about 100° C., and in the presence of an acid acceptor, for example, potassium carbonate or the like. The preferred solvent is a mixture of acetone and dimethylformamide. The resulting compound of formula Ia' can be recovered utilizing conventional methods, for example, crystallization, chromatography or the like.

A resulting compound of formula Ia' can be converted to a compound of formula Ib' by hydrolysis which is carried out with an alkali metal hydroxide, for example, sodium hydroxide, potassium hydroxide or the like, in a mixture of water and a water miscible alcohol, for example, methanol, ethanol or the like, at a temperature in the range of from about room temperature to the reflux temperature. The resulting compound of formula Ib' can be recovered utilizing conventional methods, for example, crystallization, chromatography or the like.

The starting materials of formulas III and V utilized for the preparation of the compounds of formula I can be prepared according to Reaction Schemes III, IV, V, VI, VII, VIII, IX or X which follow:

Reaction Scheme III

HAL—alkylene$_{3-7}$-HAL +

VI

-continued

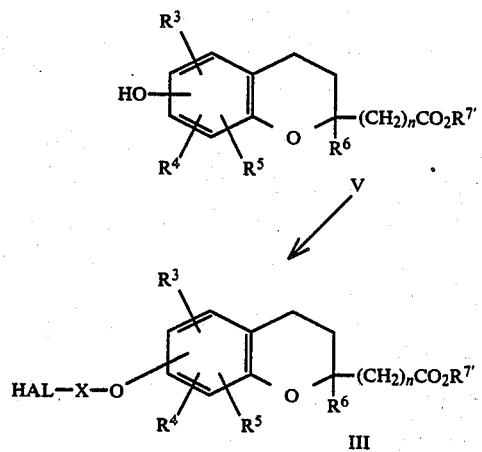

wherein $R^3$, $R^4$, $R^5$, $R^6$, $R^{7'}$, X, HAL and n are as previously described.

In Reaction Scheme III, the reaction of a compound of formula VI, which are known compounds or can be prepared according to known procedures, with a compound of formula V to yield a compound of formula III is carried out in an inert organic solvent such as dimethylformamide, acetone, methyl ethyl ketone or the like, preferred is dimethylformamide, in the presence of a base, for example, an alkali metal carbonate such as potassium carbonate, sodium carbonate or the like, or an alkali metal hydride such as sodium hydride or the like, at a temperature in the range of about 20° C. to about 150° C., preferably at room temperature. The resulting compound of formula III can be recovered utilizing conventional methods, for example, crystallization, extraction, chromatography or the like.

Reaction Scheme IV

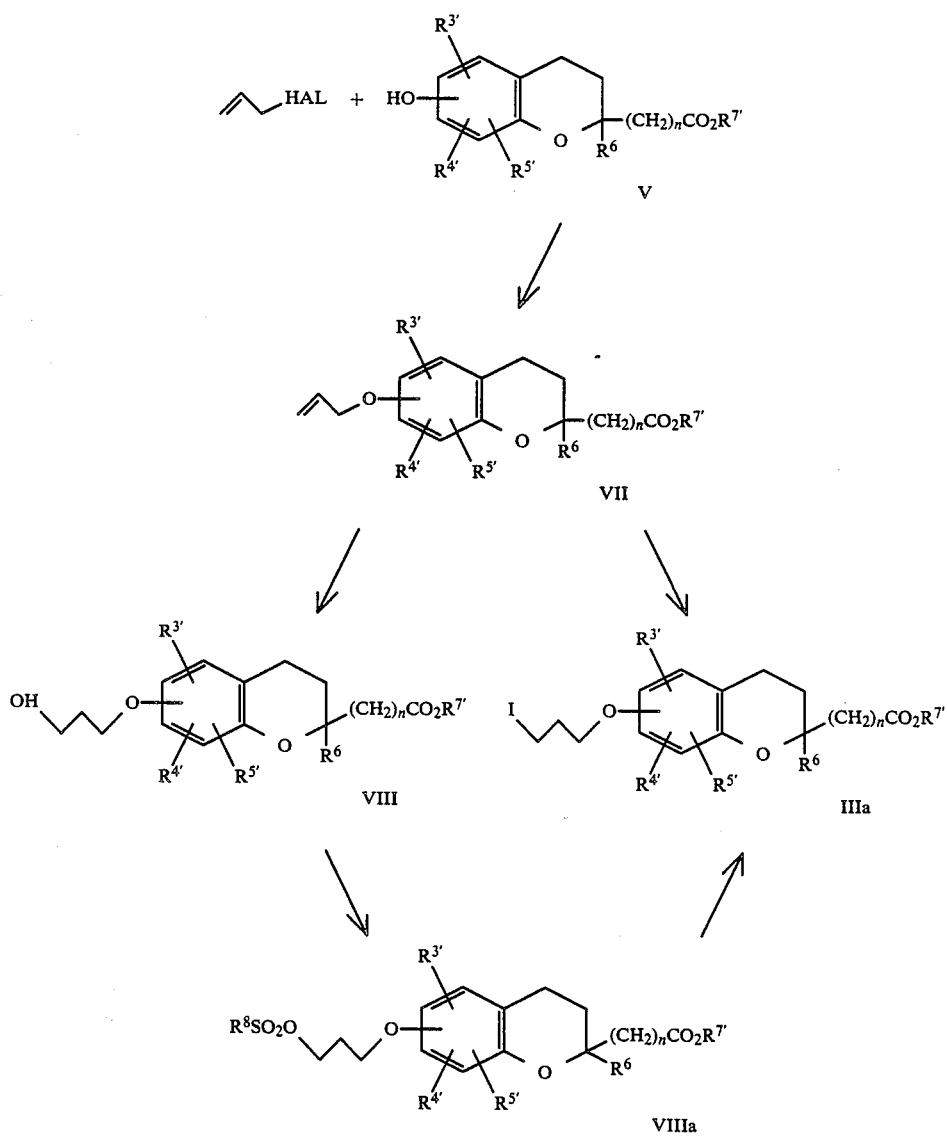

wherein $R^6$, $R^{7'}$ and n are as previously described, $R^{3'}$, $R^{4'}$ and $R^{5'}$ are hydrogen or lower alkyl, and $R^8$ is lower alkyl or aryl.

In Reaction Scheme IV, the reaction of an allyl halide, which are known compounds or can be prepared according to known procedures, is reacted with a compound of formula V to yield a compound of formula VII in an inert organic solvent such as dimethylformamide, acetone, methylethyl ketone and the like, preferred is dimethylformamide, in the presence of a base, for example, an alkali metal carbonate such as potassium carbonate, sodium carbonate or the like, or an alkali metal hydride such as sodium hydride or the like, at a temperature in the range of from about 20° C. to about 150° C., preferably at room temperature. The resulting compound of formula VII can be recovered utilizing conventional methods, for example, crystallization, extraction, chromatography or the like.

A compound of formula VII is converted to a compound of formula VIII utilizing the usual conditions for the hydroboration of an olefin. For example, utilizing a hydride of the formula $(Q)_2BH$ wherein Q is hydrogen, lower alkyl or lower cycloalkyl, preferred is borane ($BH_3$), dicyclohexylborane or borane-dimethyl sulfide complex, in an inert ether solvent, preferably tetrahydrofuran, at a temperature in the range of from about 0° C. to about 100° C., preferably at room temperature. The organoborane intermediate which is formed is oxidized, preferably by utilizing alkaline hydrogen peroxide, or the like. The resulting compound of formula VIII can be recovered utilizing conventional methods.

A compound of formula VIII is reacted with a sulfonyl chloride of the formula $R^8SO_2Cl$, wherein $R^8$ is alkyl or aryl, such as phenyl, to yield the compound of formula VIIIa utilizing conditions conventionally used for converting an alcohol to a sulfonate ester, the methanesulfonate ester is preferred. For example, the sulfonation is carried out in an inert solvent, such as dichloromethane utilizing a sulfonating agent such as alkylsulfonyl chloride, preferably methanesulfonyl chloride in the presence of a base, for example, tri-lower alkylamine, pyridine or the like, preferably triethylamine, at a temperature in the range of from about 0° C. to about 25° C., preferably at 0° C. The resulting compound of formula VIIIa can be recovered utilizing conventional methods.

A compound of formula VIIIa is converted to a compound of formula IIIa utilizing conditions conventionally used for transforming a sulfonate ester to an iodide. For example, a compound of formula VIIIa is treated with an alkali metal iodide, for example, sodium iodide, lithium iodide, potassium iodide and the like, preferably sodium iodide, in a solvent, for example, a dialkyl ketone, such as ethyl methyl ketone, acetone and the like, preferably acetone, at a temperature in the range of from about 20° C. to about 100° C., preferably at 20° C. The resulting compound of formula IIIa can be recovered utilizing conventional methods.

Alternatively, a compound of formula VII is converted to a compound of formula IIIa under conditions conventionally utilized for converting a terminal olefin to a primary iodide by hydroboration and iodination. For example, the reaction can be carried out utilizing iodine and a hydride of the formula $(Q)_2BH$ wherein Q is hydrogen, lower alkyl or lower cycloalkyl, preferred is dicyclohexylborane, in the presence of an inert ether solvent such as tetrahydrofuran and a base, for example, an alkaki metal carboxylate, preferably sodium acetate, at a temperature in the range of from about 0° C. to about 20° C. The resulting compound of formula IIIa can be recovered utilizing conventional methods.

Reaction Scheme V

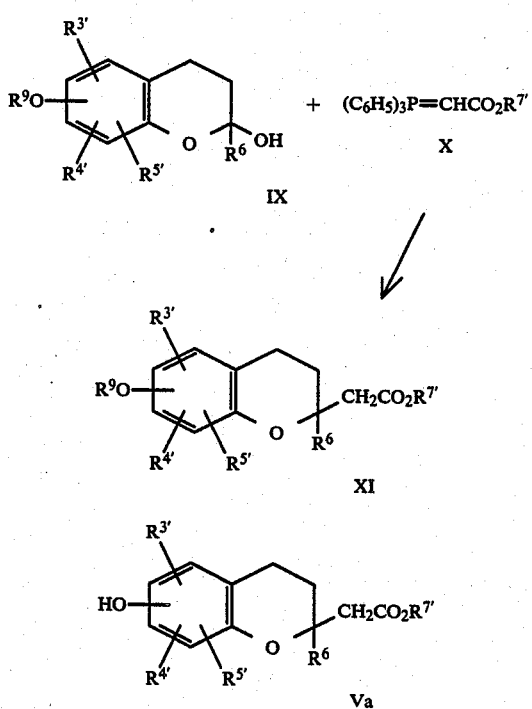

wherein $R^{3'}$, $R^{4'}$, $R^{5'}$, $R^6$ and $R^{7'}$ are as previous described, and $R^9$ is aralkyl.

In Reaction Scheme V, the reaction of a compound of formula IX with a compound of the formula $(C_6H_5)_3P=CHCO_2R^{7'}$, wherein $R^{7'}$ is lower alkyl, preferably ethyl, which are known compounds or can be prepared according to known procedures, to yield a compound of formula XI, is carried out in an inert aromatic hydrocarbon solvent, preferably toluene, at a temperature in the range of from about 20° C. to about 150° C., preferably at about 110° C. The resulting compound of formula XI can be recovered utilizing conventional methods.

A compound of formula XI can be converted to a compound of formula Va by any known method for catalytic hydrogenolysis. For example, by treatment with hydrogen in the presence of a catalyst such as palladium on carbon, in a solvent, for example, an alkanol such as ethanol, preferably at room temperature and one atmosphere of pressure. The resulting compound of formula Va can be recovered utilizing conventional methods.

Reaction Scheme VI

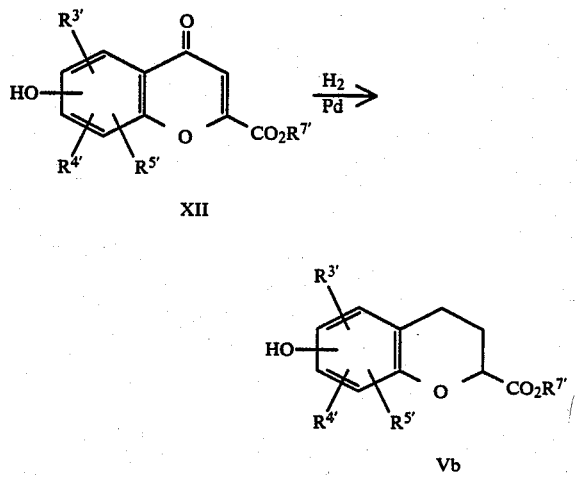

wherein $R^{3'}$, $R^{4'}$, $R^{5'}$ and $R^{7'}$ are as previously described.

In Reaction Scheme VI, a compound of formula XII, which are known compounds or can be prepared according to known procedures, is hydrogenated to yield a compound of formula Vb. More particularly, the reaction is carried out with a catalyst, for example, palladium on carbon, in a solvent such as a lower carboxylic acid, preferably acetic acid, at a temperature in the range of about 20° C. to about 150° C., preferably at 25° C., and at an increased pressure, preferably at 50 psi. The resulting compound of formula Vb can be recovered utilizing conventional methods.

Reaction Scheme VII

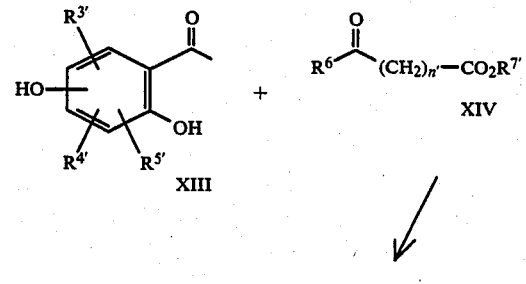

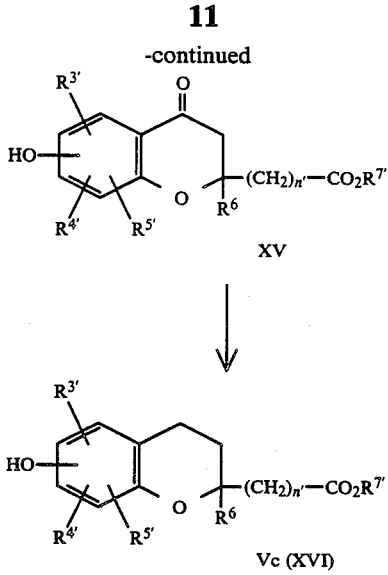

wherein $R^{3'}$, $R^{4'}$, $R^{5'}$, $R^6$ and $R^{7'}$ are as previously described, and n' is 2, 3 or 4.

In Reaction Scheme VII, a compound of formula XIII, which are known compounds can be prepared according to known procedures, is reacted with a compound of formula XIV, which are known compounds or can be prepared according to known procedures, to yield a compound of formula XV in the presence of a catalyst, for example, a cyclic secondary amine such as pyrrolidine, and an inert aromatic hydrocarbon, preferably toluene, at a temperature in the range of about 25° C. to about 150° C., preferably at 110° C. The resulting compound of formula XV can be recovered utilizing conventional methods.

A compound of formula XV is reduced to a compound of formula Vc utilizing, for example, borane in the presence of a Lewis acid such as boron trifluoride, boron trichloride, aluminum trichloride and the like, preferred is boron trifluoride etherate, and an inert ether solvent, for example, tetrahydrofuran, at a temperature in the range of about 0° C. to about 25° C., preferably at 0° C. The resulting compound of formula Vc can be recovered utilizing conventional methods.

wherein $R^{4'}$, $R^6$, $R^{7'}$ and n are as previously described, and $R^{10}$ is hydrogen or lower alkyl.

In Reaction Scheme VIII, a phenolic compound of formula XVIII is converted to its acyl derivative of formula XIX utilizing any suitable acylating agent, for example, a lower acyl halide or anhydride, preferred is acetic anhydride, in a suitable base, for example, pyridine, a lower alkylamine or the like, preferred is pyridine, at a temperature in the range of from about 0° C. to about 150° C., preferably at 25° C. The resulting compound of formula XIX can be recovered utilizing conventional methods, if desired.

A compound of formula XIX can be converted to a compound of formula Vd utilizing any conventional reaction conditions for effecting a Fries rearrangement of a phenyl acylate. For example, it can be carried out in the presence of a Lewis acid catalyst, for example, aluminum chloride, stannic chloride, boron trifluoride or the like, boron trifluoride etherate is preferred, in a solvent, for example, a halogenated hydrocarbon, lower alkanoic acid or the like, preferably in acetic acid, at a temperature in the range of from about 20° C. to about 150° C., preferably at 120° C. The resulting compound of formula Vd can be recovered utilizing conventional methods.

Alternatively, a compound of formula XVIII can be converted to a compound of formula Vd under conventional conditions for effecting a Friedel-Crafts acylation of a phenol. For example, the acylation can be carried out utilizing a Lewis acid catalyst, such as, aluminum chloride, stannic chloride, boron trifluoride or the like, preferably gaseous boron trifluoride, and an acylating agent, for example, a lower acyl halide, lower acyl anhydride, lower alkanoic acid or the like, preferably in acetic acid, at a temperature in the range of from about 20° C. to about 150° C., preferred is 80° C. The resulting compound of formula Vd can be recovered utilizing conventional methods.

Reaction Scheme VIII

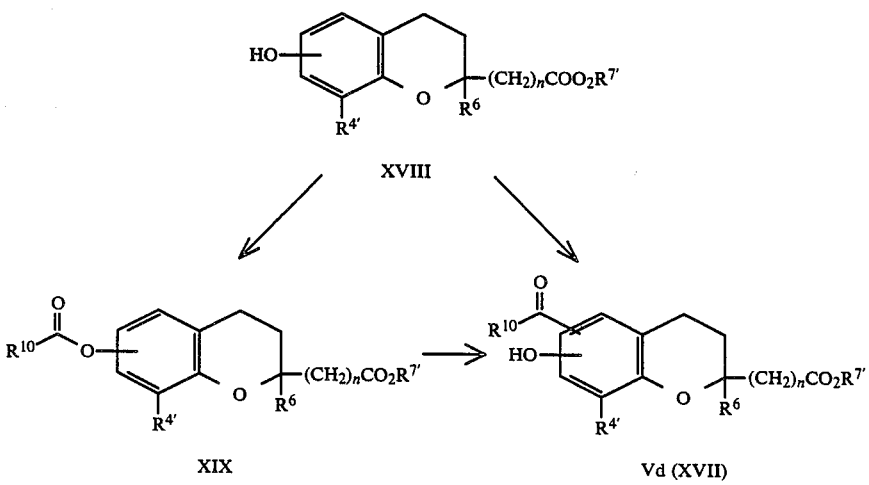

Reaction Scheme IX

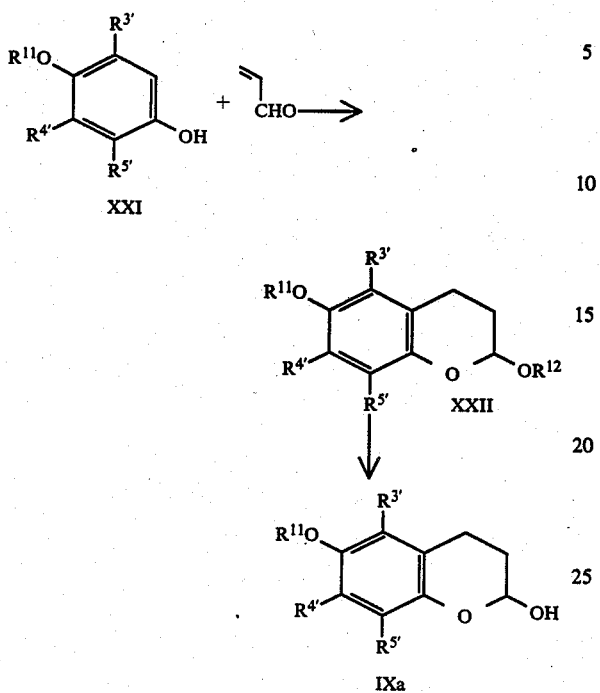

wherein $R^{3'}$, $R^{4'}$ and $R^{5'}$ are as previously described, $R^{11}$ is hydrogen or ar-lower alkyl, preferably benzyl, and $R^{12}$ is lower alkyl.

In Reaction Scheme IX, a compound of formula XXI, which are known compounds or can be prepared according to known procedures, is treated with acrolein to yield a compound of formula XXII utilizing as a catalyst, for example, a strong mineral acid such as hydrochloric acid, sulfuric acid, aryl or alkylsulfonic acid such as paratoluenesulfonic acid, or the like, preferably concentrated sulfuric acid, in a solvent, for example, a lower alkanol such as ethanol, methanol or the like, preferably methanol, at a temperature in the range of from about 20° C. to about 200° C., preferably at 150° C. The resulting compound of formula XXII can be recovered utilizing conventional methods.

A compound of formula XXII is converted to a compound of formula IXa utilizing as a catalyst a strong mineral acid such as dilute hydrochloric acid, sulfuric acid or aryl- or alkylsulfonic acid such as para-toluenesulfonic acid, or the like, preferably dilute aqueous hydrochloric acid, in an organic solvent which is miscible with water such as acetone, methanol, ethanol, tetrahydrofuran, acetic acid or the like, preferably acetone, at a temperature in the range of from about 20° C. to about 150° C., preferably at 60° C.

Reaction Scheme X

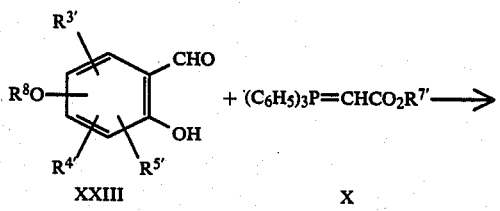

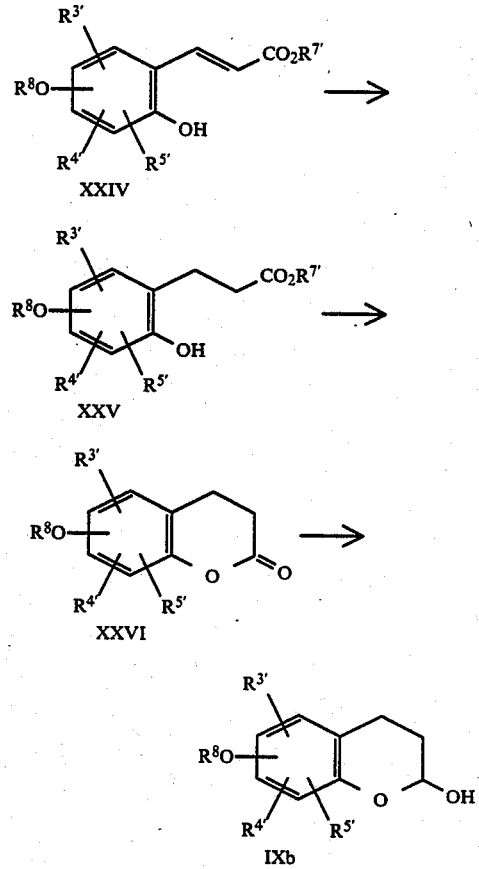

wherein $R^{3'}$, $R^{4'}$, $R^{5'}$, $R^{7'}$ and $R^8$ are as previously described.

In Reaction Scheme X, a compound of formula XXIII, which are known compounds or can be prepared according to known procedures, is reacted with a compound of formula X, which are also known compounds or can be prepared according to known procedures, to yield a compound of formula XXIV, in an inert organic ether solvent or aromatic hydrocarbon, for example, tetrahydrofuran, dioxane, glyne, benzene, toluene, xylene or the like, preferably toluene, at a temperature in the range of from about 20° C. to about 200° C., preferably at 110° C. The resulting compound of formula XXIV can be recovered utilizing conventional methods.

A compound of formula XXIV can be hydrogenated to form a compound of formula XXV utilizing a conventional catalyst for the hydrogenation, for example, palladium on carbon, platinum oxide, nickel, or the like, preferred is platinum oxide, in the presence of a solvent, for example, a lower alkanoic acid, ethyl acetate, or the like, preferably alkyl acetate, at a temperature in the range of from about 20° C. to about a 100° C., preferably 20° C., and at atmospheric pressure. The resulting compound of formula XXV can be recovered utilizing conventional methods.

A compound of formula XXV can be converted to a compound of formula XXVI by saponification which is followed by lactonization. The saponification can be carried out utilizing an alkali metal hydroxide, preferably potassium hydroxide, in a solvent, for example, a lower alcohol, preferably methanol, at a temperature in the range of from about 20° C. to about 100° C., preferably 65° C. The lactonization can be carried out, for example, with a lower alkanoic anhydride, such as, acetic anhydride, which can also be used as the solvent, at a temperature in the range of from about 20° C. to about 200° C., preferably at the boiling point of the acetic anhydride. The resulting compound of formula XXVI can be recovered utilizing conventional methods.

A compound of formula XXVI can be converted to a compound of formula IXb utilizing a conventional reducing agent, for example, a di-lower alkyl aluminum hydride, preferably diisobutylaluminum hydride, at a temperature in the range of from about −50° C. to about −100° C., preferably −75° C. in an inert solvent, for example, an aromatic hydrocarbon, chlorinated alkane, or lower alkane, preferably dichloromethane. The resulting compound of formula IXb can be recovered utilizing conventional methods.

The compounds of formula II of the invention can be prepared as hereinafter described in Reaction Schemes XI and XII.

reflux temperature of the reaction mixture, in dimethylformamide, preferably at a temperature in the range of from about 70° to about 100° C., and in the presence of an acid acceptor, for example, potassium carbonate or the like. The preferred solvent is a mixture of acetone and dimethylformamide. The resulting compound of formula IIa can be recovered utilizing conventional methods, for example, crystallization, chromatography or the like.

A compound of formula IIa can be converted to a compound of formula IIb by hydrolysis which is carried out with an alkali metal hydroxide, for example, lithium hydroxide, sodium hydroxide, potassium hydroxide or the like, in a mixture of water and a water miscible solvent, for example, methanol, ethanol, tetrahydrofuran or the like, at a temperature in the range of from about room temperature to the reflux temperature. The resulting compound of formula IIb can be recovered utilizing conventional methods, for example, crystallization, chromatography or the like.

Reaction Scheme XI

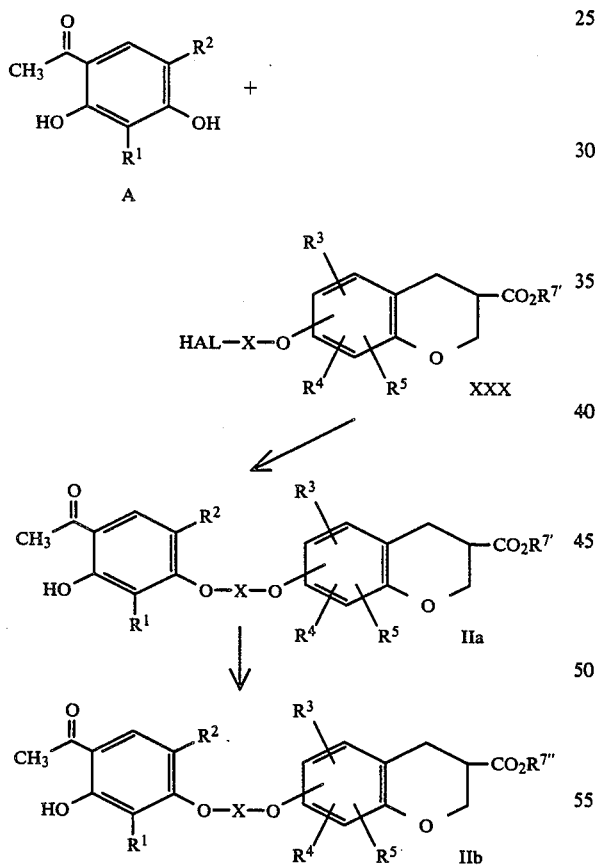

Reaction Scheme XII

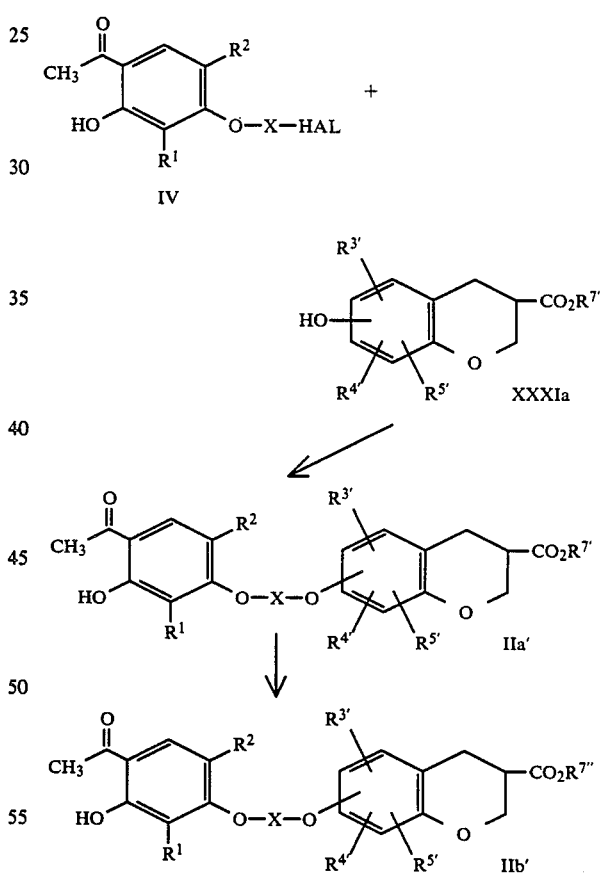

wherein $R^1$, $R^2$, $R^3$, $R^4$, $R^5$ and X are as previously described, $R^{7'}$ is lower alkyl, $R^{7''}$ is hydrogen and HAL is halogen.

In Reaction Scheme XI, the reaction of a compound of formula A, which are known compounds or can be prepared according to known procedures, with a compound of formula XXX to yield a compound of formula IIa is carried out under anhydrous conditions in an inert solvent, for example, acetone, methylethyl ketone, diethyl ketone, dimethylformamide or the like, at the wherein $R^1,R^2,R^{3'},R^{4'},R^{5'},R^{7'},R^{7''}$,HAL and X are as previously described.

In Reaction Scheme XII, a compound of formula IV is reacted with a compound of formula XXXIa to yield a compound of formula IIa', which is subsequently converted to a compound of formula IIb', as hereinbefore described in connection with Reaction Scheme II.

The starting materials of formulas XXX and XXXIa which are utilized in Reaction Schemes XI and XII for the preparation of the compounds of formula II can be prepared according to Reaction Schemes XIII, XIV and XV.

Reaction Scheme XIII

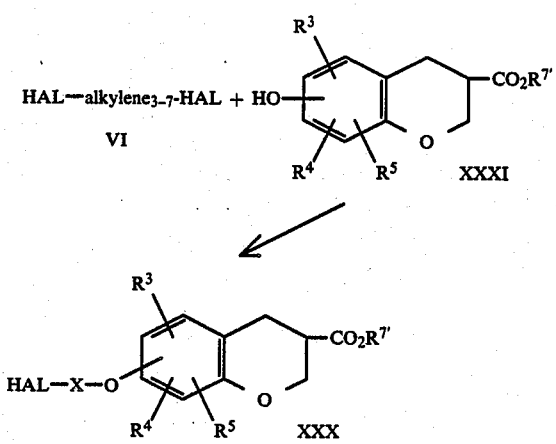

wherein $R^3, R^4, R^5, R^{7'}, X$ and HAL are as previously described.

In Reaction Scheme XIII, the reaction of a compound of formula VI, which are known compounds or can be prepared according to known procedures, with a compound of formula XXXI to yield a compound of formula XXX is carried out in an inert organic solvent such as dimethylformamide, acetone, methyl ethyl ketone or the like, preferred is dimethylformamide, in the presence of a base, for example, an alkali metal carbonate such as potassium carbonate, sodium carbonate or the like, or an alkali metal hydride such as sodium hydride or the like, at a temperature in the range of about 20° C. to about 150° C., preferably at room temperature. The resulting compound of formula XXX can be recovered utilizing conventional methods, for example, crystallization, extraction, chromatography or the like.

Reaction Scheme XIV

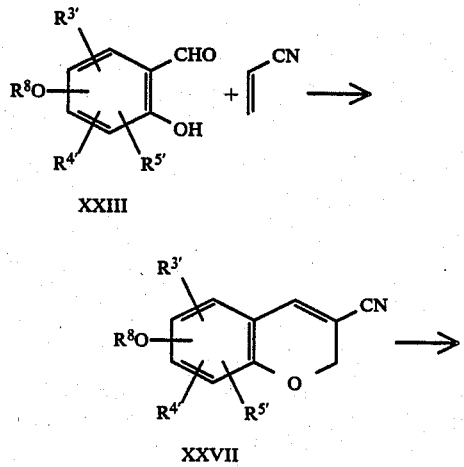

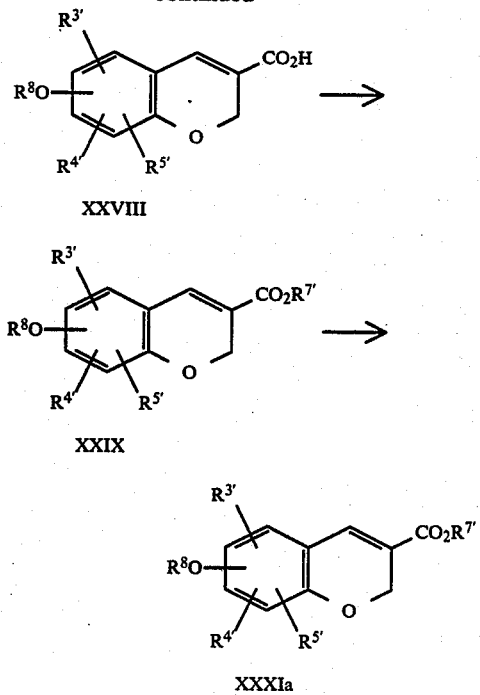

wherein $R^{3'}, R^{4'}, R^{5'}, R^{7'}$ and $R^8$ are as previously described.

In Reaction Scheme XIV, a compound of formula XXIII is reacted with acrylonitrile to yield a compound of formula XXVII. The reaction is carried out in the presence of a catalyst, for example, an aromatic amine, such as, triethylamine, diazabicycloundecene, diazabicyclo(2.2.2)octane is preferred, at a temperature in the range of about 20° C. to about 100° C., preferably 80° C., without solvent. The resulting compound of formula XXVII can be recovered utilizing conventional methods.

A compound of formula XXVII is converted to a compound of formula XXVIII by saponification, for example, with an alkali metal hydroxide, such as, potassium hydroxide, in a solvent, such as a water miscible organic solvent, for example, tetrahydrofuran, methanol, ethanol, or the like, preferably ethanol or tetrahydrofuran, at a temperature in the range of about 20° C. to about 100° C., preferably at 60° C. to 70° C. The resulting compound of formula XXVIII can be recovered utilizing conventional methods.

The conversion of a compound of formula XXVIII to a compound of formula XXIX can be carried out by an esterification utilizing a lower alkanol as a reagent and a solvent, for example, ethanol, at a temperature in the range of about 20° C. to about 100° C., preferably at 78° C., in the presence of a catalyst, for example, a strong acid, such as, sulfuric acid, para-toluenesulfonic acid, or the like, preferably paratoluenesulfonic acid. The resulting compound of formula XXIX can be recovered utilizing conventional methods.

A compound of formula XXIX can be converted to a compound of formula XXXIa by catalytic hydrogenation, for example, utilizing palladium on a support, nickel, platinum, preferably palladium on carbon in the presence of a solvent, for example, a lower alkanol, acetic acid, ethyl acetate, or the like, preferably ethanol, at a temperature in the range of from about 20° C.–200°

C., preferably at 20° C., to one atmosphere of pressure. The resulting compound of formula XXXIa can be recovered utilizing conventional methods.

Reaction Scheme XV

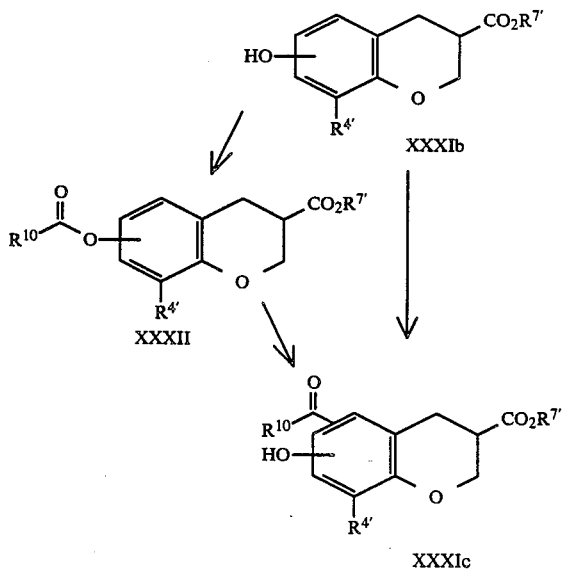

wherein $R^{4'}, R^{7'}$ and $R^{10}$ are as previously described.

In Reaction Scheme XV, a compound of the formula XXXIb can be converted to a compound of formula XXXIc directly or via compound XXXII as described above in Reaction Scheme VIII for the conversion of XVIII to Vd.

Reaction Scheme XVI

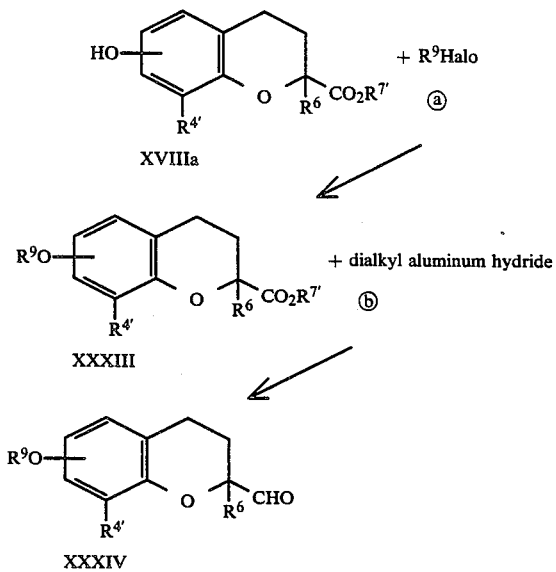

Wherein $R^{4'}, R^{6}, R^{7'}$ and $R^{9}$ are as previously described, and Halo is halogen.

In Reaction Scheme XVI, the reaction of a compound of formula XVIIIa, with a compound of formula (a) to yield a compound of formula XXXIII is carried out under anhydrous conditions in an inert solvent, for example, acetone, methylethyl ketone, diethyl ketone, dimethylformamide or the like, at the reflux temperature of the reaction mixture, preferably at a temperature in the range of from about 40° to about 100° C., and in the presence of an acid acceptor, for example, potassium carbonate or the like. The preferred solvent is acetone. The resulting compound of formula XXXIII can be recovered utilizing conventional methods, for example, crystallization, chromatography or the like.

A compound of formula XXXIII can be converted to a compound of formula XXXIV utilizing a conventional reducing agent, for example, a di-lower alkyl aluminum hydride, preferably diisobutylaluminum hydride, at a temperature in the range of from about −50° C. to about −100° C., preferably −75° C. in a inert solvent, for example, an aromatic hydrocarbon, chlorinated alkane, or lower alkane, preferably toluene. The resulting compound of formula XXXIV can be recovered utilizing conventional methods.

Reaction Scheme XVII

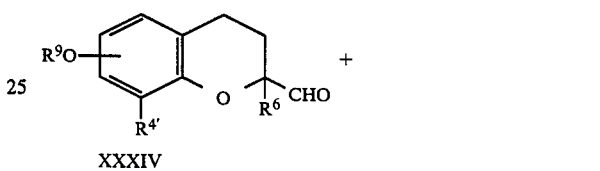

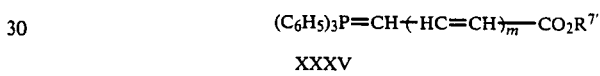

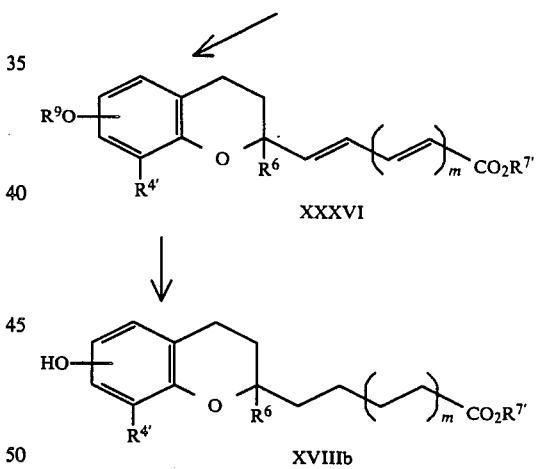

Wherein m is 0 or 1, and $R^{4'}, R^{6}, R^{7'}$ and $R^{9}$ are as previously described.

In Reaction Scheme XVII, the reaction of a compound of formula XXXIV with a compound of the formula $(C_6H_5)_3 P=CH(CH=CH)_m CO_2R^{7'}$, wherein $R^{7'}$ is lower alkyl, preferably ethyl, and m is 0 or 1, which are known compounds or can be prepared according to known procedures, to yield a compound of formula XXXVI, is carried out in an inert aromatic hydrocarbon solvent, preferably toluene, at a temperature in the range of from about 20° C. to about 150° C., preferably at about 110° C. The resulting compound of formula XXXVI can be recovered utilizing conventional methods.

A compound of formula XXXVI can be converted to a compound of formula XVIIIb by any known method for catalytic hydrogenation. For example, by treatment with hydrogen in the presence of a catalyst such as palladium on carbon, in a solvent, for example, an alkanol such as ethanol or ethyl acetate, preferably at room temperature and one atmosphere of pressure. The resulting compound of formula XVIIIb can be recovered utilizing conventional methods.

This invention also relates to the pharmaceutically acceptable salts of the 3,4-dihydro-2H-1-benzopyran derivatives of formulas I and II and their enantiomers, when $R^7$ is hydrogen. Said salts can be prepared by reacting an acid of formula I or II or an enantiomer thereof with a base having a non-toxic, pharmacologically and pharmaceutically acceptable cation. In general, any base which will form a salt with a carboxylic acid and whose pharmacological properties will not cause an adverse physiological effect when ingested by a warm-blooded animal is considered as being within the scope of the invention. Suitable bases thus includes, for example, alkali metal and alkaline earth metal hydroxides or carbonates, such as, sodium hydroxide, potassium hydroxide, calcium hydroxide, potassium carbonate and the like, ammonia, primary, secondary and tertiary amines, such as monoalkylamines, dialkylamines, trialkylamines, nitrogen containing heterocyclic amines, for example, piperidine, basic amino acids such as lysine, and the like. The pharmaceutically acceptable salts thus produced are the functional equivalent of the corresponding 3,4-dihydro-2H-1-benzopyran acids of formula I and II and their enantiomers and one skilled in the art will appreciate that, to the extent that the salts of the invention are useful in therapy, the variety of salts encompassed by this invention are limited only by the criterion that the bases employed in forming the salts be both non-toxic and physiologically acceptable.

The useful antiallergic activity of the compounds of formulas I and II, and enantiomers thereof is demonstrated in vitro and in warm-blooded animals utilizing standard pharmacological procedures. Exemplary of such procedures are:

(a) Guinea Pig Ileum, In Vitro:

The guinea pig ileum bioassay system has been described by Orange Austen, Adv. Immunol. 10: 105-144 (1969). A 1.5 cm segment is removed from animals weighing 300-400 g and suspended in an organ bath containing 10 ml of Tyrodes solution with $10^{-6}$M atropine sulfate and $10^{-6}$M pyrilamine maleate. The bath is maintained at 37° C. and aerated with a mixture of 95% oxygen and 5% carbon dioxide. The SRS-A utilized in this screen is obtained by challenging chopped lung fragments from actively sensitized guinea pigs with egg albumin, in vitro. A dose-response curve to SRS-A challenge is established for the ileum. The dose of SRS-A which gives 50% of the maximal contraction ($EC_{50}$) is then used for subsequent challenge. The drug concentration which inhibits, by 50%, the SRS-A-induced constriction of the guinea pig ileum is determined. In this bioassay system, the standard SRS-A antagonist, 7-[3-(4-acetyl-3-hydroxy-2-propylphenoxy)-2-hydroxypropoxy]-4-oxo-8-propyl-4H-1-benzopyran-2-carboxylic acid, has an $IC_{50}$ of $3.5 \times 10^{-8}$M.

(b) Guinea Pig Bronchoconstriction, In Vivo (Aerosol):

Male guinea pigs (Hartley strain) weighing 300 to 500 g are anesthetized with urethane (2 g/kg) intraperitoneally and a polyethylene cannula is inserted into the jugular vein for drug administration. Tracheal pressure is recorded from a cannula inserted in the trachea and connected to a Statham pressure transducer. After surgical preparation of the animals, a period of time is allowed for pulmonary functions to stabilize. The test compound is administered according to the following protocol. Propanolol (0.1 mg/kg) is administered intravenously while the animals breathed spontaneously. Five minutes thereafter, the animals are exposed for a five minute period to a 1% (w/v) aerosol solution of test compound (adjusted to an alkaline pH where necessary for drug solubilization) or to distilled water of the appropriate pH (for control purposes). A Monaghan (Model 750) ultrasonic nebulizer is used to administer all test compounds by inhalation. The nebulizer ultrasonic frequency is adjusted to produce particles in the 1-8$\mu$ diameter range (average 3$\mu$). Aqueous solutions are prepared freshly and introduced into the chamber of the nebulizer. The output of the nebulizer is made available to the animal by directing a bias flow of aerosol through a Y tube connected to the tracheal cannula. At the end of the exposure period, the animals are paralyzed with succinylcholine (1.2 mg/kg, i.v.) and mechanically respirated (Harvard rodent respirator) at 40 breaths/minute and 2.5 cc tidal volume. Animals are then challenged with a maximum constrictory dose of leukotriene $E_4$ delivered intravenously 30 seconds after administration of the succinylcholine.

The change (cm $H_2O$) between pre and peak ventilatory pressure readings averaged for three control animals and five drug treated animals. The percent inhibition is calculated from the following formula:

$$\frac{\text{Control} - \text{Drug Treated}}{\text{control}} \times 100$$

When various drug concentrations are tested, the percent inhibition at each concentration is plotted as log concentration (abscissa) versus percent inhibition (ordinate) and the $IC_{50}$ is determined from linear regression analysis.

When compounds of formulas I and II, as listed hereinafter in Table I, were utilized in the test procedures described above the result set out in Table I were obtained:

TABLE I

| | SRS-A ANTAGONISM | |
|---|---|---|
| Test Compound | In vitro Guinea Pig ileum $IC_{50}$(M) | Guinea Pig Bronchoconstriction In vivo aerosol - $IC_{50}$(%) |
| rac-6-[3-(4-Acetyl-3-hydroxy-2-propylphenoxy)propoxy]-3,4-dihydro-2,5,7,8-tetramethyl-2H—1-benzopyran-2-carboxylic acid | $1 \times 10^{-7}$ | 1.0 |
| rac-7-[3-(4-Acetyl-3-hydroxy-2-propylphenoxy)propoxy]-3,4-dihydro-2-methyl-2H—1-benzopyran-2-propanoic acid | $1 \times 10^{-7}$ | >1.0 |
| rac-6-[3-(4-Acetyl-3-hydroxy-2- | $2 \times 10^{-7}$ | 1.0 |

TABLE I-continued

SRS-A ANTAGONISM

| Test Compound | In vitro Guinea Pig ileum IC$_{50}$(M) | Guinea Pig Bronchoconstriction In vivo aerosol - IC$_{50}$(%) |
|---|---|---|
| propylphenoxy)propoxy]-3,4-dihydro-2,5,7,8-tetramethyl-2H—1-benzopyran-2-acetic acid | | |
| rac-7-[3-(4-Acetyl-3-hydroxy-2-propylphenoxy)propoxy]-3,4-dihydro-2-methyl-8-propyl-3H—1-benzopyran-2-propanoic acid | 5 × 10$^{-7}$ | 0.71 |
| rac-6-[3-(4-Acetyl-3-hydroxy-2-propylphenoxy)propoxy]-3,4-dihydro-2-methyl-2H—1-benzopyran-2-carboxylic acid | 1 × 10$^{-7}$ | 0.20 |
| rac-6-[3-(4-Acetyl-3-hydroxy-2-propylphenoxy)-propoxy]-3,4-dihydro-2-methl-2H—1-benzopyran-2-propanoic acid | 5 × 10$^{-7}$ | >1.0 |
| rac-6-Acetyl-7-[3(4-acetyl-3-hydroxy-2-propylphenoxy)propoxy-2-methyl-propyl-2H—1-benzopyran-2-propanoic acid | 8 × 10$^{-8}$ | 0.12 |
| rac-6-[3-(4-Acetyl-3-hydroxy-2-propylphenoxy)-propoxy]-3,4-dihydro-5,7,8-trimethyl-2H—1-benzopyran-2-carboxylic acid | 1 × 10$^{-7}$ | 1.0 |
| rac-7-[3-(4-Acetyl-3-hydroxy-2-propylphenoxy)propoxy]-3,4-dihydro-2H—1-benzopyran-2-acetic acid | 1 × 10$^{-7}$ | 0.67 |
| rac-6-[3-(4-Acetyl-3-hydroxy-2-propylphenoxy)propoxy]-3,4-dihydro-2H—1-benzopyran-2-acetic acid | 4 × 10$^{-7}$ | 1.0 |
| rac-6-[3-(4-Acetyl-3-hydroxy-2-propylphenoxy)propoxy]-3,4-dihydro-2H—1-benzopyran-2-carboxylic acid | 5 × 10$^{-7}$ | 0.50 |
| rac-7-[3-(4-Acetyl-3-hydroxy-2-propylphenoxy)-propoxy]-3,4-dihydro-8-propyl-2H—benzopyran-2-carboxylic acid | 1 × 10$^{-7}$ | 0.20 |
| rac-7-[3-(4-Acetyl-3-hydroxy-2-propylphenoxy)propoxy]-3,4-dihydro-2H—1-benzopyran-2-carboxylic acid | 6 × 10$^{-8}$ | 0.14 |
| rac-7-[3-(4-Acetyl-3-hydroxy-2-propylphenoxy)propoxy]-3,4-dihydro-2H—1-benzopyran-3-carboxylic acid | 1 × 10$^{-7}$ | >1.0 |
| rac-6-Acetyl-7-[3-(4-acetyl-3-hydroxy-2-propylphenoxy)propoxy]-3,4-dihydro-2H—1-benzopyran-2-carboxylic acid | 1 × 10$^{-7}$ | 0.20 |
| rac-6-Acetyl-7-[3-(4-acetyl-3-hydroxy-2-propylphenoxy)propoxy]-3,4-dihydro-8-propyl-2H—1-benzopyran-2-carboxylic acid | 1 × 10$^{-7}$ | 0.38 |
| rac-7-Acetyl-6-[3-(4-acetyl-3-hydroxy-2-propylphenoxy)propoxy]-3,4-dihydro-2H—1-benzopyran-2-carboxylic acid | 2 × 10$^{-7}$ | 0.34 |
| rac-6-Acetyl-7-[5-(4-acetyl-3-hydroxy-2-propylphenoxy)pentyloxy]-3,4-dihydro-2H—1-benzopyran-2-carboxylic acid | 6 × 10$^{-8}$ | 0.052 |
| rac-6-Acetyl-7-[[7-(4-acetyl-3-hydroxy-2-propylphenoxy)heptyl]oxy]-3,4-dihydro-2H—1-benzopyran-2-carboxylic acid | 1 × 10$^{-6}$ | 1.0 |
| rac-8-Acetyl-7-[3-(4-acetyl-3-hydroxy-2-propylphenoxy)propoxy]-3,4-dihydro-2H—1-benzopyran-2-carboxylic acid | 3 × 10$^{-7}$ | 0.59 |
| rac-7-Acetyl-6-[3-(4-acetyl-3-hydroxy-2-propylphenoxy)propoxy]-3,4-dihydro-2-methyl-2H—1-benzopyran-2-carboxylic acid | 5 × 10$^{-7}$ | 1.0 |

When in the above aerosol assay procedure leukotriene E$_4$ was replaced with leukotriene D$_4$, racemic-6-acetyl-7-[5-(4-acetyl-3-hydroxy-2-propylphenoxy)pentyloxy]-3,4-dihydro-2H-1-benzopyran-2-carboxylic acid was found to exhibit an IC$_{50}$ value of 0.0056% in inhibiting bronchoconstriction; (R)-(−)-6-acetyl-7-[5-(4-acetyl-3-hydroxy-2-propylphenoxy)pentyloxy]-3,4-dihydro-2H-1-benzopyran-2-carboxylic acid was found to exhibit an IC$_{50}$ value of 0.018% of inhibiting bronchoconstriction; and (S)-(+)-6-acetyl-7-[5-(4-acetyl-3-hydroxy-2-propylphenoxy)pentyloxy]-3,4-dihydro-2H-1-benzopyran-2-carboxylic acid was found to exhibit an IC$_{50}$ value of 0.0018% in inhibiting bronchoconstriction.

TABLE I

SRS A: Antagonism

| Test Compound | In Vitro Guinea Pig ileum IC$_{50}$ (M) |
|---|---|
| rac-7-[5-(4-acetyl-3-hydroxy-2-propylphenoxy)pentyloxy]-3,4-dihydro-2H—1-benzopyran-2-carboxylic acid | 2 × 10$^{-6}$ |

TABLE I-continued

SRS A: Antagonism

| Test Compound | In Vitro Guinea Pig ileum $IC_{50}$ (M) |
|---|---|
| rac-6-acetyl-7-[5-(4-acetyl-3-hydroxyphenoxy)pentyloxy]-3,4-dihydro-8-propyl-2H—1-benzopyran-2-carboxylic acid | $1 \times 10^{-6}$ |
| rac-6-acetyl-7-[5-(4-acetyl-3-hydroxyphenoxy)pentyloxy]-3,4-dihydro-2H—1-benzopyran-2-carboxylic acid | $3 \times 10^{-6}$ |
| rac-6-acetyl-7-[5-(4-acetyl-3-hydroxy-2-propylphenoxy) = pentyloxy]-3,4-dihydro-8-propyl-2H—1-benzopyran-2-carboxylic acid | $5 \times 10^{-7}$ |
| rac-6-[5-(4-acetyl-3-hydroxy-2-propylphenoxy)pentyloxy]-3,4-dihydro-2,5,7,8-tetramethyl-2H—1-benzopyran-2-carboxylic acid | $1 \times 10^{-7}$ |
| rac-7-[5-(4-acetyl-3-hydrophenoxy)pentyloxy]-3,4-dihydro-2H—1-benzopyran-2-carboxylic acid | $5 \times 10^{-6}$ |
| rac-6-acetyl-7-[6-(4-acetyl-3-hydroxy-2-propylphenoxy) = hexyloxy]-3,4-dihydro-2H—1-benzopyran-2-carboxylic acid | $3 \times 10^{-6}$ |
| rac-6-acetyl-7-[4-(4-acetyl-3-hydroxy-2-propylphenoxy) = butoxy]-3,4-dihydro-2H—1-benzopyran-2-carboxylic acid | $2 \times 10^{-6}$ |
| rac-7-[5-(4-acetyl-3-hydroxyphenoxy)pentyloxy)-3,4-dihydro-8-propyl-2H—1-benzopyran-2-carboxylic acid | $6 \times 10^{-6}$ |
| rac-7-[5-(4-acetyl-3-hydroxy-2-propylphenoxy)pentyloxy]-3,4-dihydro-8-propyl-2H—1-benzopyran-2-carboxylic acid | $8 \times 10^{-7}$ |
| (+)-(R)—6-[5-(4-acetyl-3-hydroxy-2-propylphenoxy) = pentyloxy]-3,4-dihydro-2,5,7,8-tetramethyl-2H—1-benzopyran-2-carboxylic acid | $5 \times 10^{-7}$ |
| (−)-(S)—6-[5-(4-acetyl-3-hydroxy-2-propylphenoxy)pentyloxy]-3,4-dihydro-2,5,7,8-tetramethyl-2H—1-benzopyran-2-carboxylic acid | $8 \times 10^{-7}$ |
| (S)—6-acetyl-7-[ 5-(4-acetyl-3-hydroxy-2-propylphenoxy) = pentyloxy]-3,4-dihydro-2H—1-benzopyran-2-carboxylic acid | $6 \times 10^{-8}$ |
| (R)—6-acetyl-7-[5-(4-acetyl-3-hydroxy-2-prophylphenoxy) = pentyloxy]-3,4-dihydro-2H—1-benzopyran-2-carboxylic acid | $1 \times 10^{-7}$ |

(c) Oral Testing of Leukotriene Antagonists

Male guinea pigs (Hartley strain, Charles River) weighing 400 to 600 g were anesthetized with urethane (2 g/kg) intraperitoneally and a polyethylene cannula was inserted into the jugular vein for intravenous drug administration. Tracheal pressure (cm water) was recorded from a Statham pressure transducer. After surgical preparation of the animals, a period of time was allowed for spontaneous breathing to stabilize. Since previous studies have demonstrated a potentiating effect of propanolol (0.1 mg/kg, i.v.) on bronchoconstriction induced with synthetic leukotriene, propanolol was administered five minutes prior to challenge with leukotriene. Two minutes later, spontaneous breathing was arrested with succinylcholine chloride (1.2 mg/kg, i.v.) and the animals ventilated with a Harvard (Model #680) small animal respirator set at 40 breaths per minute and 4.0 cc stroke volume. The animals were challenged with a maximum constrictory does of either leukotriene $C_4$ or leukotriene $D_4$ or leukotriene $E_4$ (25 ug/kg, i.v.) at 5 minutes. Control vehicle or test drug (adjusted to an alkaline pH where necessary for drug solubilization) was administered (10 mg/kg, p.o.) two hours prior to challenge with leukotriene. In order to determine the $ID_{50}$ for a test drug, the dose is varied from 10 mg/kg, p.o. to 100, 50, 30, 20, 5, 3 and 1 mg/kg, p.o.

In order to determine oral duration of action, the time between exposure to test drug and challenge with leukotriene is varied.

In test procedure (c), of the compounds tesed by this oral procedure, racemic-6-acetyl-7-[5-(4-acetyl-3-hydroxy-2-propylphenoxy)pentyloxy]-3,4-dihydro-2H-1-benzopyran-2-pentanoic acid exhibited 46±14% inhibition of leukotriene $D_4$ induced bronchoconstriction when administered at 10 mg/kg by the oral route.

A compound of formula I or II, an enantiomer thereof or a salt thereof, when $R^7$ is hydrogen, or a composition containing a therapeutically effective amount of a compound of formula I or II, an enantiomer thereof or a salt thereof, when $R^7$ is hydrogen, can be administered by methods well known in the art. Thus, a compound of formula I or II, an enantiomer thereof or a salt thereof, when $R^7$ is hydrogen, can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example, in the form of an aerosol, micropulverized powder or nebulized solution. Presently, the most preferred route of administration for the compounds of formula I or II is by inhalation, for example, as an aerosol, and particularly for use as an antiasthmatic agent. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound of formula I or II, an enantiomer thereof, or a salt thereof, when $R^7$ is hydrogen, to be administered and the frequency of administration will be dependent on the potency and duration of activity of the particular compound of formula I or II, an enantiomer or salt thereof to be administered and on the route of administration, as well as the severity of the condition, age of the warm-blooded animal to be treated and the like. Doses of a compound of formula I or II, an enantiomer thereof or a salt thereof, when $R^7$ is hydrogen, contemplated for use in the practice of the invention are in the range of from about 25 to about 1000 mg per day, preferably about 25 to about 250 mg either as a single dose or in divided doses per day.

Since the compounds of formulas I and II of the invention possess an asymmetric carbon atom, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture of a compound of formula I or II, when $R^7$ is hydrogen, with an optically active resolving agent, for example, an optically active base, such as d-(+)-α-methylbenzylamine, which can be reacted with a carboxyl group. The formed diastereomers are separated by selective crystallization and converted to the corresponding optical isomer. Thus, the invention covers the racemates of the compounds of formulas I and II, as well as their optically active isomers (enantiomers).

Alternatively, resolution can be achieved by treatment of the corresponding acid of an ester of formula V or XXX with an optically active amine resolving agent such as (R)- or (S)-alpha methylbenzylamine, (R)- or (S)-alphanaphthylethyl amine, quinine, quinidine, ephedrine and the like, preferably (R)- or (S)-alpha methylbenzylamine. After separation of the diastereomeric salts as described above, the optically active acid obtained is recovered by acid treatment and converted, after conversion to the corresponding ester, into the corresponding optically active compound of formula I or II, as described for the preparation of the racemic series.

In addition, resolution can be achieved by treatment of the corresponding acid of an ester of formulas III, V, XXX or XXXI with an optically active alcohol to produce a mixture of diastereomeric esters which can be separated by crystallization or chromatography. Representative optically active alcohol resolving agents are menthol, borneol, 2-octanol, 2,3-butanediol, and the like. The preferred mode of resolution involves the mono-ester of 2R,3R-butanediol and acids derived from esters of formulas III, V, XXX or XXXI. These esters can be formed using conventional methods. The preferred method is conventional Fisher esterification using a strong acid catalyst. The preferred acid catalyst is para-toluenesulfonic acid. The diastereomeric esters from the acids of formulas III or XXX can be formed by alkylation of the corresponding diastereomeric esters from formulas V or XXXI with a dihaloalkane of formula VI, using conventional techniques described above. The preferred chromatographic technique for achieving the resolution is high performance liquid chromatography (HPLC). After separation, the resolved diastereomeric esters from acids of formulas III and XXX are converted into the corresponding resolved acids of formulas Ib' and IIb' using conventional techniques described above for the racemic compounds.

In the following examples, all reactions were carried out under an inert atmosphere (argon). The "usual work-up" or "processing in the usual manner" involves three extractions with the specified solvent. The organic extracts were then combined, washed with water and brine, dried over anhydrous magnesium sulfate, filtered and concentrated under water aspirator pressure. The residue was dried to constant weight at 40°-50° C./high vacuum. Column chromatography was carried out using silica gel 0.063-0.2 mm.

The examples which follow also further describe the invention. All temperatures given are in degree centigrade almost otherwise stated.

EXAMPLE 1

A mixture of 30.4 g of 2',4'-dihydroxyacetophenone, 28.8 g of ethyl levulinate, 21.3 g of pyrrolidine, and 400 ml of toluene was stirred and refluxed for 3 hours with removal of water by means of a Dean-Stark trap. The resulting mixture was cooled in an ice bath and treated with 300 ml of 1.2N aqueous hydrochloric acid. After being stirred at room temperature for 45 minutes, the mixture was treated with ether and the aqueous layer was separated. The organic solution was washed with 1.2N hydrochloric acid. The aqueous acidic solutions were combined and extracted twice with ether. The organic solutions were combined, washed with water, saturated aqueous sodium bicarbonate and brine, then dried (magnesium sulfate), filtered and concentrated under reduced pressure. The residual red oil (42 g) was chromatographed on 400 g of silica gel. Elution with 9:1 toluene-ethyl acetate gave 32.3 g (58.1%) of racemic-3,4-dihydro-7-hydroxy-2-methyl-4-oxo-2H-1-benzopyran-2-propanoic acid ethyl ester as an orange, viscous oil.

EXAMPLE 2

To a stirred solution of 1.5 g of racemic-3,4-dihydro-7-hydroxy-2-methyl-4-oxo-2H-1-benzopyran-2-propanoic acid ethyl ester in 8 ml of dry tetrahydrofuran, with ice bath cooling, was added 1.4 ml of boron trifluoride etherate, over a period of 2 minutes. The mixture was stirred at 0°-5° C. for 5 minutes whereupon 5.4 ml of 1M borane in tetrahydrofuran was added. Stirring was continued at 0°-5° C. for 2.5 hours then the mixture was decomposed by the addition of glacial acetic acid. Solvents were removed in vacuo then the residue was dissolved in methylene chloride. The solution was washed with sodium bicarbonate solution and brine, then dried, filtered and concentrated under reduced pressure. The residual orange oil (1.4 g) was chromatographed on 50 g of silica gel. Elution with 4:1 hexane-ethyl acetate afforded 0.9 g (63.1%) of racemic-3,4-dihydro-7-hydroxy-2-methyl-2H-1-benzopyran-2-propanoic acid ethyl ester as a colorless oil.

Analysis Calculated for $C_{15}H_{20}O_4$: C, 68.16; H, 7.63. Found: C, 67.86; H, 7.60.

EXAMPLE 3

To a stirred slurry of 120 mg of 50% sodium hydride-mineral oil dispersion in 0.5 ml of dry N,N-dimethylformamide was added a solution of 292 mg of racemic-3,4-dihydro-7-hydroxy-2-methyl-2H-1-benzopyran-2- propanoic acid ethyl ester in 3 ml of dry N,N-dimethylformamide. The mixture was stirred at room temperature for 25 minutes at which point a solution of 364 mg of 4'-(3-bromopropoxy)-2'-hydroxy-3'-n-propylacetophenone in 3 ml of dry N,N-dimethylformamide was added. After being stirred at room temperature for 21 hours, the mixture was treated with ether and dilute hydrochloric acid and worked-up with ether in the usual manner giving 523 mg of an orange oil. This material was chromatographed on 50 g of silica gel. Elution with 19:1 toluene-ethyl acetate afforded 257 mg (46.5%) of racemic-7-[3-(4-acetyl-3-hydroxy-2-propylphenoxy)propoxy]-3,4-dihydro-2-methyl-2H-1-benzopyran-2-propanoic acid ethyl ester as a pale yellow oil.

Analysis Calculated for $C_{29}H_{38}O_7$: C, 69.86; H, 7.68. Found: C, 69.65; H, 7.73.

EXAMPLE 4

To a mixture of 1.55 g of the ester from Example 3 and 35 ml of 1:1 tetrahydrofuran-water was added 2.3 g of lithium hydroxide monohydrate, with stirring. The mixture was stirred at room temperature for 22 hours then diluted with water and extracted 3 times with ether (ether extracts discarded). The aqueous solution was acidified to pH 1 by the addition of saturated aqueous oxalic acid and worked-up with ether in the usual manner. There was obtained 1.4 g (95.8%) of racemic-7-[3-(4-acetyl-3-hydroxy-2-propylphenoxy)propoxy]-3,4-dihydro-2-methyl-2H-1-benzopyran-2-propanoic acid as a viscous yellow oil.

Analysis Calculated for $C_{27}H_{34}O_7$; C, 68.92, H, 7.28. Found: C, 68.62; H, 7.23.

EXAMPLE 5

A mixture of 3.88 g of 2',4'-dihydroxy-3'-n-propylacetophenone, 3.17 g of ethyl levulinate, 0.83 ml of pyrrolidine, and 20 ml of toluene was stirred at room temperature for 1 hour then refluxed for 3 hours with water removal using a Dean-Stark trap. The resulting dark red-brown mixture was cooled, treated with 25 ml of 1N hydrochloric acid, and stirred at room temperature for 30 minutes. Water was added and the mixture was worked-up with ether in the usual manner giving 5.1 g of a dark red oil. This material was chromatographed on 100 g of silica gel. Elution with 9:1 and 4:1 toluene-ethyl acetate afforded 2.9 g (45.3%) of racemic-3,4-dihydro-7-hydroxy-2-methyl-4-oxo-3-n-propyl-2H-1-benzopyran-2-propanoic acid ethyl ester as a yellow oil.

Analysis Calculated for $C_{18}H_{24}O_5$: C, 67.48; H, 7.55. Found: C, 67.31; H, 7.54.

EXAMPLE 6

Using the procedure of Example 2, 257 mg of racemic-3,4-dihydro-7-hydroxy-2-methyl-4-oxo-8-n-propyl-2H-1-benzopyran-2-propanoic acid ethyl ester was reduced with borane.tetrahydrofuran and boron trifluoride etherate. There was obtained 195 mg of racemic-3,4-dihydro-7-hydroxy-2-methyl-8-n-propyl-2H-1-benzopyran-2-propanoic acid ethyl ester as a pale yellow oil, after chromatographic purification on silica gel.

Analysis Calculated for $C_{18}H_{26}O_4$: C, 70.56; H, 8.55. Found: C, 70.01; H, 8.28.

EXAMPLE 7

To a stirred slurry of 108 mg of 50% sodium hydride-mineral oil dispersion (prewashed with hexane) in 1 ml of anhydrous N,N-dimethylformamide was added a solution of 268 mg of racemic-3,4-dihydro-7-hydroxy-2-methyl-3-n-propyl-2H-1-benzopyran-2-propanoic acid ethyl ester in 3 ml of dry N,N-dimethylformamide at room temperature, over a 1 minute period. After being stirred for 30 minutes at room temperature, the mixture was treated dropwise with a solution of 313 mg of 4'-(3-bromopropoxy)-2'-hydroxy-3'-n-propylacetophenone in 3 ml of dry N,N-dimethylformamide. Sodium iodide (0.3 g) was added and the mixture was stirred at room temperature for 2.5 hours before being quenched with 1 ml of water. After 30 minutes, 0.3 g of lithium hydroxide monohydrate and 1 ml of water were added and stirring was continued for 3 hours. The mixture was acidified to pH 1 with 1N hydrochloric acid and worked-up with ether in the usual manner. The orange oily product (0.7 g) was chromatographed on 50 g of silica gel. Elution with 4:1 toluene-ethyl acetate gave 310 mg (69.1%) of racemic-7-[3-(4-acetyl-3-hydroxy-2-n-propylphenoxy)propoxy]-3,4-dihydro-2-methyl-8-n-propyl-2H-1-benzopyran-2-propanoic acid as a viscous yellow oil after drying at 60° C. under high vacuum.

Analysis Calculated for $C_{30}H_{40}O_7$: C, 70.29; H, 7.87. Found: C, 70.19; H, 7.99.

EXAMPLE 8

Using the procedure of Example 1, 15 g of 2',5'-dihydroxyacetophenone was condensed with 14.2 g of ethyl levulinate and 12.3 ml of pyrrolidine, in 200 ml of toluene. The crude product (20.5 g) was purified by high pressure liquid chromatography (silica gel; 2:1 hexane-ethyl acetate) giving 17.6 g (64.1%) of racemic-3,4-dihydro-6-hydroxy-2-methyl-4-oxo-2H-1-benzopyran-2-propanoic acid ethyl ester as a yellow oil.

Analysis Calculated for $C_{15}H_{18}O_5$: C, 64.74; H, 6.52. Found: C, 64.28; H, 6.64.

EXAMPLE 9

To a solution of 8.25 g of racemic-3,4-dihydro-6-hydroxy-2-methyl-4-oxo-2H-1-benzopyran-2-propanoic acid ethyl ester in 50 ml of dry glyme was added 7.29 ml of boron trifluoride etherate dropwise with stirring and ice bath cooling. After being stirred at 0°-5° C. for 10 minutes, the mixture was treated with 1.75 g of boranedimethylamine complex. Stirring was continued for 1 hour at room temperature at which point 5 ml of glacial acetic acid was added and the solution was poured into cold water and worked-up with ether in the usual manner (the combined organic extracts were additionally washed with sodium bicarbonate solution). The crude product was found to contain a substantial amount of the starting ketone and was resubjected to the foregoing reduction procedure and work-up. There was obtained 8.1 g of a yellow oil which was purified by preparative high pressure liquid chromatography (silica gel, 2:1 hexane-ethyl acetate) giving 5.8 g (74.1%) of racemic-3,4-dihydro-6-hydroxy-2-methyl-2H-1-benzopyran-2-propanoic acid ethyl ester as a yellow oil.

EXAMPLE 10

Utilizing the procedure of Example 7, 0.695 g of racemic-3,4-dihydro-6-hydroxy-2-methyl-2H-1-benzopyran-2-propanoic acid ethyl ester was alkylated with 0.939 g of 4'-(3-bromopropoxy)-2'-hydroxy-3'-n-propylacetophenone using sodium hydride and sodium iodide in dry N,N-dimethylformamide. After saponification (1.25 g of lithium hydroxide monohydrate), there was obtained 1.4 g of crude acid. Column chromatography on silica gel (50 g) afforded 0.837 g (67%) of racemic-6-[3-(4-acetyl-3-hydroxy-2-propylphenoxy)-propoxy]-3,4-dihydro-2-methyl-2H-1-benzopyran-2-propanoic acid as a colorless oil (eluted with 9:1 and 4:1 toluene-ethyl acetate).

Analysis Calculated for $C_{27}H_{34}O_7$: C, 68.92; H, 7.28. Found: C, 68.36; H, 7.20.

EXAMPLE 11

The procedure of Example 7 was employed to alkylate 0.9 g of the ethyl ester of racemic-3,4-dihydro-6-hydroxy-2-methyl-2H-1-benzopyran-2-carboxylic acid with 4'-(3-bromopropoxy)-2'-hydroxy-3'-n-propylacetophenone (1.5 g), using sodium hydride (12.16 mmole), and sodium iodide (10 mmoles), in N,N-dimethylformamide. After saponification with lithium hydroxide monohydrate (1.5 g), the crude acid product was purified by chromatography on silica gel. There was obtained 1.16 g (68.9%) of racemic-6-[3-(4-acetyl-3-hydroxy-2-propylphenoxy)propoxy]-3,4-dihydro-2-methyl-2H-1-benzopyran-2-carboxylic acid as an off-white solid mp 108°–110.5° C.

Analysis Calculated for $C_{25}H_{30}O_7$: C, 67.86; H, 6.83. Found: C, 67.92; H, 6.97.

EXAMPLE 12

A 365 mg portion of 50% sodium hydride-mineral oil dispersion was washed with hexane and suspended in 32 ml of anhydrous N,N-dimethylformammide. To the stirred slurry was added 1 g of racemic-3,4-dihydro-2,5,7,8-tetramethyl-6-hydroxy-2H-1-benzopyran-2-carboxylic acid methyl ester. After being stirred at room temperature for 45 minutes, the mixture was treated dropwise with 3.2 ml (4.47 g) of allyl bromide. Stirring was continued for 90 hours at room temperature at which point 3 ml of methanol was added. The mixture was poured into water and worked-up with ether in the usual manner giving 1.8 g of an amber oil. This material was purified by column chromatogrpahy on silica gel and then preparative high pressure liquid chromatography (silica gel, 19:1 hexane-ethyl acetate). There was obtained 772 mg (67.2%) of racemic-3,4-dihydro-2,5,7,8-tetramethyl-6-(2-propenyloxy)-2H-1-benzopyran-2-carboxylic acid methyl ester as a pale-yellow oil. This material was evaporatively distilled, bp 105°–107° C. (bath temperature) (0.02 mm), giving an oil which crystallized on standing to a solid, mp 68°–70° C.

Analysis Calculated For $C_{18}H_{24}O_4$: C, 71.03; H, 7.95. Found: C, 71.37; H, 7.90.

EXAMPLE 13

To a solution of 1.8 g of racemic-3,4-dihydro-2,5,7,8-tetramethyl-6-(2-propenyloxy)-2H-1-benzopyran-2-carboxylic acid methyl ester in 36 ml of anhydrous tetrahydrofuran was added 1.98 ml of borane-dimethyl sulfide with stirring and ice bath cooling. The reaction mixture was stirred for 1.5 hours at 0°–5° C., then decomposed by the dropwise addition of 9 ml of water. After being stirred at 0°–5° C. for 10 minutes, the mixture was treated dropwise with 6.84 ml of 3N sodium hydroxide followed by 2.2 ml of 30% hydrogen peroxide. The mixture was stirred at 5°–10° C. for 1 hour then acidified with 7 ml of 3N hydrochloric acid. Work-up with ether in the usual manner gave 2 g of an oil which was purified by preparative HPLC (silica gel, 1:1 hexane-ethyl acetate). There was obtained 1.22 g (64%) of racemic-3,4-dihydro-2,5,7,8-tetramethyl-6-(3-hydroxypropoxy)-2H-1-benzopyran-2-carboxylic acid methyl ester as a cololess oil.

Analysis Calculated for $C_{18}H_{26}O_5$: C, 67.06; H, 8.13. Found: C, 67.39; H, 8.19.

EXAMPLE 14

To a solution of 0.3 g of racemic-3,4-dihydro-2,5,7,8-tetramethyl-6-(3-hydroxypropoxy)-2H-1-benzopyran-2-carboxylic acid methyl ester in 5 ml of anhydrous methylene chloride and 0.33 ml of triethylamine was added 0.17 ml of methanesulfonyl chloride. The mixture was stirred at room temperature for 45 minutes then treated with 1N sulfuric acid and worked-up with methylene chloride in the usual manner. There was obtained 0.461 g of racemic-3,4-dihydro-2,5,7,8-tetramethyl-6-(3-methanesulfonyloxypropoxy)-2H-1-benzopyran-2-carboxylic acid methyl ester as an oil which was used without further purification.

EXAMPLE 15

A mixture of the crude methanesulfonate from Example 14 (about 0.932 mmole), 595 mg of sodium iodide, and 5 ml of acetone was stirred at room temperature for 43.5 hours then treated with water and worked-up with ether in the usual manner (the ether extracts were additionally washed with dilute sodium bisulfite solution). The oily product (390 mg) was chromatographed on 20 g of silica gel. Elution with 19:1 and 9:1 hexane-ethyl acetate afforded 306 mg (76.0%) of racemic-3,4-dihydro-2,5,7,8-tetramethyl-6-(3-iodopropoxy)-2H-1-benzopyran-2-carboxylic acid methyl ester as a colorless oil. In another experiment, iodide prepared in this way crystallized to a solid, mp 73°–75.5° C.

EXAMPLE 16

A mixture of 0.137 g of 2',4'-dihydroxy-3'-n-propylacetophenone, 0.195 g of anhydrous potassium carbonate, and 3 ml of anhydrous N,N-dimethylformamide was stirred for 1 hour at room temperaure. A solution of the iodide from Example 15 (0.306 g) in 5 ml of N,N-dimethylformamide was added and the mixture was stirred for 30 minutes at room temperature and at 60° C. for 31 hours. After being cooled, the reaction mixture was treated with 1N hydrochloric acid and worked-up with ether in the usual manner. The oily product (0.406 g) was chromatographed on 20 g of silica gel. Elution with 4:1 hexane-ethyl acetate gave 0.291 g (82.5%) of racemic-6-[3-(4-acetyl-3-hydroxy-2-propylphenoxy)propoxy]-3,4-dihydro-2,5,7,8-tetramethyl-2H-1-benzopyran-2-carboxylic acid methyl ester as a pale-yellow oil. In another experiment, material prepared in this way crystallized and afforded a colorless solid mp 121°–123° C. (from ethanol).

Analysis Calculated for $C_{29}H_{38}O_7$: C, 69.86; H, 7.68. Found: C, 69.31; H, 7.67.

EXAMPLE 17

A solution of 0.246 g of the methyl ester from Example 16, and 0.227 g of sodium hydroxide in 8 ml of methanol and 2 ml of water was stirred at room temperature for 1.5 hours then treated with 1N hydrochloric acid and worked-up with ether in the usual manner. The crude product was redissolved in ether and the solution was washed with dilute sodium bicarbonate solution. The aqueous alkaline phase was acidified with 2N hydrochloric acid and worked-up with ether in the usual manner giving 0.161 g (67.3%) of acid as a yellow oil which crystallized on standing. Recrystallization from benzene-hexane gave racemic-6-[3-(4-acetyl-3-hydroxy-2-propylphenoxy)propoxy]-3,4-dihydro-2,5,7,8-tetramethyl-2H-1-benzopyran-2-carboxylic acid as a colorless solid, mp 137°–139° C.

Analysis Calculated for $C_{28}H_{36}O_7$: C, 69.40; H, 7.49. Found: C, 69.28; H, 7.58.

EXAMPLE 18

Using the procedure of Example 12, 1.42 g of racemic-3,4-dihydro-2,5,7,8-tetramethyl-6-hydroxy-2H-1-benzopyran-2-acetic acid methyl ester was alkylated with allyl bromide (2.79 g) and sodium hydride (5.58 mmole) in anhydrous N,N-dimethylformamide. There was obtained 1.35 g (83.1%) of racemic-3,4-dihydro-2,5,7,8-tetramethyl-6-(2-propenyloxy)-2H-1-benzopyran-2-acetic acid methyl ester as a yellow oil, after column chromatographic purification (silica gel, 9:1 hexane-ethyl acetate).

Analysis Calculated for $C_{19}H_{26}O_4$: C, 71.67; H, 8.23. Found: C, 71.54; H, 8.25.

EXAMPLE 19

To a stirred, ice-cold solution of 1M borane in tetrahydrofuran (10 ml) was added, dropwise, a solution of 2 ml (1.64 g) of cyclohexene in 6 ml of dry tetrahydrofuran. The mixture was allowed to stir at 0°–5° C. for 1.5 hours. To the resulting slurry of dicyclohexylborane was added, dropwise a solution of 1.59 g of the allyl ether from Example 18 in 4 ml of tetrahydrofuan. The mixture was stirred at 0°–5° C. for 1 hour and at room temperature for 18 hours at which point 20 ml of 1M methanolic sodium acetate was added dropwise followed by 23.8 ml of 0.4M methanolic iodine. The resulting mixture was stirred at room temperature for 4 hours whereupon 3.1 ml of aqueous sodium thiosulfate was added. The reaction mixture was poured into water and worked-up with ether in he usual manner. Chromatography of the crude product (4.4 g) on 100 g of silica gel afforded 1.71 g (76.7%) of racemic-3,4-dihydro-6-(3-iodopropoxy)-2,5,7,8-tetramethyl-2H-1-benzopyran-2-acetic acid methyl ester as an oil, eluted with 19:1 and 9:1 hexane-ethyl acetate.

EXAMPLE 20

Using the procedure of Example 16, 328 mg of 2',4'-dihydroxy-3'-n-propylacetophenone was alkylated with 756 mg of the iodide from Example 19, and anhydrous potassium carbonate (467 mg), in anhydrous N,N-dimethylformamide. There was obtained 0.789 g (91.1%) of racemic-6-[3-(4-acetyl-3-hydroxy-2-propylphenoxy)-propoxy]-3,4-dihydro-2,5,7,8-tetramethyl-2H-1-benzopyran-2-acetic acid methyl ester as a yellow oil after column chromatography (silica gel, 4:1 hexane-ether).

EXAMPLE 21

A 0.669 g sample of the methyl ester from Example 20 was saponified with sodium hydroxide using the procedure described in Example 17. The crude acid product was chromatographed on 30 g of silica gel. Elution with 2:1 hexane-ethyl acetate afforded 0.386 g (59.6%) of racemic-6-[3-(4-acetyl-3-hydroxy-2-propylphenoxy)propoxy]-3,4-dihydro-2,5,7,8-tetramethyl-2H-1-benzopyran-2-acetic acid as a yellow glass.

Analysis Calculated for $C_{29}H_{38}O_7$: C, 69.86; H, 7.68. Found: C, 69.63; H, 7.89.

EXAMPLE 22

To a stirred solution of 0.8 g of racemic-3,4-dihydro-7-hydroxy-2-methyl-8-n-propyl-2H-1-benzopyran-2-propanoic acid ethyl ester in 8 ml of pyridine was added 0.37 ml of acetic anhydride. The solution was stirred at room temperature for 5 hours then poured into ice-water and worked up with ether in the usual manner (the combined ether extracts were additionally washed with 1N hydrochloric acid and saturated sodium bicarbonate solutions). The oily product (1.0 g) was chromatographed on 50 g of silica gel. Elution with 19:1 toluene-ethyl acetate afforded 0.575 g (63.3%) of racemic-7-acetoxy-3,4-dihydro-2-methyl-8-n-propyl-2H-1-benzopyran-2-propanoic acid ethyl ester as a pale-yellow oil.

Analysis Calculated for $C_{20}H_{28}O_5$: C, 68.94; H, 8.10. Found: C, 68.73; H, 8.06.

EXAMPLE 23

To a stirred solution of 276 mg of racemic-7-acetoxy-3,4-dihydro-2-methyl-8-n-propyl-2H-1-benzopyran-2-propanoic acid ethyl ester in 2 ml of glacial acetic acid was added 0.21 ml of boron trifluoride etherate, at room temperature. The mixture was stirred at 105° C. for 24 hours then cooled and diluted with ether. The ether solution was washed with water and brine and processed in the usual manner given 298 mg of a yellow-brown oil. This material was chromatographed on 30 g of silica gel. Elution with 4:1 toluene-ethyl acetate afforded 183 mg (72.1%) of racemic-6-acetyl-3,4-dihydro-7-hydroxy-2-methyl-8-n-propyl-2H-1-benzopyran-2-propanoic acid as an off-white solid, mp 154°–156° C.

Analysis Calculated for $C_{18}H_{24}O_5$: C, 67.48; H, 7.55. Found: C, 67.17; H, 7.72.

EXAMPLE 24

A solution of 692 mg of racemic-6-acetyl-3,4-dihydro-7-hydroxy-2-methyl-8-n-propyl-2H-1-benzopyran-2-propanoic acid and 100 mg of p-toluenesulfonic acid monohydrate in 10 ml of absolute ethanol was stirred and refluxed for 17 hours. The resulting solution was cooled and treated with a small amount of saturated sodium bicarbonate then concentrated in vacuo to remove the ethanol. The residue was treated with ether and the ether solution was processed in the usual manner given 752 mg of a yellow oil. This material was chromatographed on 50 g of silica gel. Elution with 4:1 toluene-ethyl acetate provided 706 mg (92.9%) of racemic-6-acetyl-3,4-dihydro-7-hydroxy-2-methyl-8-n-propyl-2H-1-benzopyran-2-propanoic acid ethyl ester as a yellow oil.

Analysis Calculated for $C_{20}H_{28}O_5$: C, 68.94; H, 8.10. Found: C, 68.86; H, 7.85.

EXAMPLE 25

A mixture of 263 mg of racemic-6-acetyl-3,4-dihydro-7-hydroxy-2-methyl-8-n-propyl-2H-1-benzopyran-2-propanoic acid ethyl ester, 222 mg of anhydrous potassium carbonate, 0.39 ml of 1,3-dibromopropane, 6 ml of anhydrous acetone, and 3 ml of anhydrous N,N-dimethylformamide was stirred and refluxed for 16 hours. An additional 0.25 g of anhydrous potassium carbonate was added and stirring, and refluxing were continued for 25 hours. The mixture was cooled and volatile materials were removed first under water aspirator pressure and then high vacuum. The residue was treated with ether and acetone and the solids were removed by filtration. Concentration of the filtrate in vacuo afforded 359 mg of racemic-6-acetyl-7-(3-bromopropoxy)-3,4-dihydro-2-methyl-8-n-propyl-2H-1-benzopyran-2-propanoic acid ethyl ester as an orange oil.

EXAMPLE 26

A mixture of 335 mg of racemic-6-acetyl-7-(3-bromopropoxy)-3,4-dihydro-2-methyl-8-n-propyl-2H-1-benzopyran-2-propanoic acid ethyl ester, 143 mg of 2',4'-dihydroxy-3'-n-propylacetophenone, 217 mg of anhydrous potassium carbonate, 6 ml of anhydrous acetone, and 3 ml of anhydrous N,N-dimethylformamide was stirred and refluxed for 17 hours. An additional 100 mg of potassium carbonate was added and stirring, and refluxing were continued for 4 hours. After being cooled to room temperature, the mixture was cautiously acidified to pH 1 by the addition of 1N hydrochloric acid. Water was added and the mixture was worked-up with ether in the usual manner. The residue was chromatographed on 50 g of silica gel. Elution with 9:1 toluene-ethyl acetate afforded 219 mg (52.6%) of racemic-6-acetyl-7-[3-(4-acetyl-3-hydroxy-2-n-propylphenoxy)propoxy]-3,4-dihydro-2-methyl-8-n-propyl-2H-1-benzopyran-2-propanoic acid ethyl ester as a yellow oil.

EXAMPLE 27

A 191 mg sample of the product from Example 26 was saponified with lithium hydroxide monohydrate, (273 mg) in 5 ml of 3:2 tetrahydrofuran-water, using the procedure described in Example 4. After column chromatography on silica gel, racemic-6-acetyl-7-[3-(4-acetyl-3-hydroxy-2-n-propylphenoxy)propoxy]-3,4-dihydro-2-methyl-8-n-propyl-2H-1-benzopyran-2-propanoic acid was obtained as a yellow, viscous oil.

Analysis Calculated for $C_{32}H_{42}O_8$: C, 69.29; H, 7.63. Found: C, 69.07; H, 7.79.

EXAMPLE 28

An 809 mg sample of the ethyl ester of racemic-3,4-dihydro-6-hydroxy-5,7,8-trimethyl-2H-1-benzopyran-2-carboxylic acid was alkylated with 1.2 g of 4'-(3-bromopropoxy)-2'-hydroxy-3'-n-propylacetophenone, 448 mg of 50% sodium hydride-mineral oil dispersion, and 1.2 g of sodium iodide in anhydrous dimethylformamide, using the procedure of Example 7. After saponification (1.2 g of lithium hydroxide monohydrate), there was obtained 1.6 g of crude, crystalline acid. The material was chromatographed on 50 g of silica gel. Elution with 4:1, 2:1, and 1:1 toluene-ethyl acetate gave 1.2 g (83.2%) of racemic-6-[3-(4-acetyl-3-hydroxy-2-propylphenoxy)-propoxy]-3,4-dihydro-5,7,8-trimethyl-2H-1-benzopyran-2-carboxylic acid as an off-white solid, mp 144°–147° C.

Analysis Calculated for $C_{27}H_{34}O_7$: C, 68.92; H, 7.28. Found: C, 68.68; H, 7.02.

EXAMPLE 29

A mixture of 25 g of p-benzyloxyphenol, 20 ml of freshly distilled acrolein, 70 ml of methanol, and 0.5 ml of concentrated sulfuric acid was heated at 150° C. in a pressure bottle, with stirring for 2 hours. The mixture was cooled and diluted with ether. The ethereal solution was washed with water and saturated sodium bicarbonate solution and processed in the usual manner. The brown, oily residue (47.9 g) was chromatographed on 250 g of silica gel. Elution with toluene gave 23.1 g of an orange oil which was rechromatographed on 300 g of silica gel. Elution with 9:1 hexane-ethyl acetate afforded 12.8 g (37.9%) of racemic-3,4-dihydro-2-methoxy-6-(phenylmethoxy)-2H-1-benzopyran as a yellow oil. This material was dissolved in 200 ml of acetone and 120 ml of 2N aqueous hydrochloric acid was added. The mixture was stirred and refluxed for 2 hours, kept overnight at room temperature, and refluxed for an additional 2 hours. After being cooled, the mixture was concentrated under aspirator pressure to remove most of the acetone. The aqueous residue was worked-up with ether in the usual manner (the combined ether extracts were additionally washed with saturated sodium bicarbonate solution) giving 12.1 g of a pale-yellow solid. This material was chromatographed on 250 g of silica gel. Elution with 9:1 and 4:1 toluene-ethyl acetate afforded 9.8 g (80.7%) of racemic-3,4-dihydro-6-(phenylmethoxy)-2H-1-benzopyran-2-ol as a pale-yellow solid, mp 92.5°–95° C.

Analysis Calculated for $C_{16}H_{16}O_3$: C, 74.98; H, 6.29. Found: C, 74.78; H, 6.41.

EXAMPLE 30

A solution of 1.8 g of racemic-3,4-dihydro-6-(phenylmethoxy)-2H-1-benzopyran-2-ol and 2.6 g of (carbethoxymethylene)triphenylphosphorane in 20 ml of toluene was stirred and refluxed for 22 hours. The solution was cooled and placed on a column of 50 g of silica gel packed in toluene. Elution with toluene and 19:1 toluene-ethyl acetate gave 1.7 g (74.2%) of racemic-3,4-dihydro-6-(phenylmethoxy)-2H-1-benzopyran-2-acetic acid ethyl ester as a pale-yellow oil. This material was dissolved in 25 ml of absolute ethanol and the solution was stirred in the presence of 0.2 g of 10% palladium on carbon, at room temperature, in an atmosphere of hydrogen. After 1.5 hours, hydrogen uptake ceased and the catalyst was removed by filtration. The filtrate was concentrated in vacuo to give 1.2 g (97.6%) of racemic-3,4-dihydro-6-hydroxy-2H-1-benzopyran-2-acetic acid ethyl ester as a pale-yellow oil.

EXAMPLE 31

A mixture of 1.2 g of racemic-3,4-dihydro-6-hydroxy-2H-1-benzopyran-2-acetic acid ethyl ester, 1.8 g of 4'-(3-bromopropoxy)-2'-hydroxy-3'-n-propylacetophenone, 1.6 g of anhydrous potassium carbonate, 30 ml of dry acetone, and 15 ml of dry dimethylformamide was stirred and refluxed for 23 hours. An additional 1.6 g of potassium carbonate was added and the mixture was stirred and refluxed for an additional 2.5 hours. After being cooled, the mixture was cautiously poured into 1N aqueous hydrochloric acid. Work-up with ether in the usual manner (the combined ether extracts were additionally washed with saturated aqueous sodium bicarbonate) gave 3.7 g of a brown oil which was chromatographed on 50 g of silica gel. Elution with 19:1 toluene-ethyl acetate afforded 1.6 g of a pale-yellow oil. A solution of this ester and 3.0 g of lithium hydroxide monohydrate in 40 ml of 1:1 tetrahydrofuran-water was stirred at room temperature for 23 hours. The resulting solution was diluted with water and acidified to pH 1 with 2N hydrochloric acid. Work-up with ether in the usual manner gave an oil which was chromatographed on 50 g of silica gel. Elution with 4:1, 2:1, and 1:1 toluene-ethyl acetate afforded 831 mg (37%) of racemic-6-[3-(4-acetyl-3-hydroxy-2-propylphenoxy)propoxy]-3,4-dihydro-2H-1-benzopyran-2-acetic acid as a pale-yellow solid, mp 102.5°–105° C.

Analysis Calculated for $C_{25}H_{30}O_7$: C, 67.86; H, 6.83. Found: C, 68.03; H, 6.75.

EXAMPLE 32

A mixture of 17.5 g of (carbethoxymethylene)triphenylphosphorane and 11.4 g of 4-benzyloxy-2-hydroxybenzaldehyde in 200 ml of toluene was stirred and refluxed for 1 hour. After evaporation of the solvent in vacuo, a residue of 28.2 g was obtained which contained (4'-benzyloxy-2'-hydroxy)benzenepropenoic acid ethyl ester and triphenylphosphine oxide. This material was dissolved in 300 ml of ethyl acetate and hydrogenated at atmospheric pressure and room temperature in the presence of 0.35 g of platinum oxide. The catalyst was removed by filtration and the filtrate was concentrated in vacuo giving 28.1 g of product containing (4'-benzyloxy-2'-hydroxy)benzenepropanoic acid ethyl ester. This material was treated with 100 ml of 5% methanolic potassium hydroxide solution and the mixture was refluxed for 2 hours. Most of the methanol was removed by concentration in vacuo and the residue was partitioned between ether and water. The ether layer was discarded. The aqueous phase was acidified with 2N hydrochloric acid and worked-up with 1:1 ether-tetrahydrofuran in the usual manner affording 9.8 g of (4'-benzyloxy-2'-hydroxy)benzenepropanoic acid. This material was dissolved in 98 ml of acetic anhydride and the solution was refluxed for 2 hours. After being cooled, the solution was treated with 100 ml of methanol and the solvents were removed by concentration in vacuo. The methanol treatment and evaporation were repeated twice more and the residue was purified by high pressure liquid chromatography on silica gel (eluting solvent system 4:1 hexane-ethyl acetate). There was obtained 6.2 g (48.8%) of 3,4-dihydro-7-(phenylmethoxy)-1-benzopyran-2-one as a solid.

EXAMPLE 23

To a stirred solution of 6.2 g of 3,4-dihydro-7-(phenylmethoxy)-1-benzopyran-2-one in 80 ml of dichloromethane was added dropwise 20 ml of diisobutylaluminum hydride solution (25% in toluene), at −76° C. The reaction mixture was stirred at this temperature for 1 hour whereupon 5 ml of methanol was cautiously added. The solution was poured into 25 ml of 1N sulfuric acid and the mixture worked-up with ether in the usual manner (the combined organic extracts were additionally washed with saturated sodium bicarbonate solution). The residue (5.9 g) was purified by high pressure liquid chromatography on silicagel (eluting solvent system 3:1 hexane-ethyl acetate. This afforded 4.8 g (76.8%) of racemic-3,4-dihydro-7-(phenylmethoxy)-2H-1-benzopyran-2-ol as a colorless solid, mp 64°–65.5° C.

Analysis Calculated for $C_{16}H_{16}O_3$: C, 74.98; H, 6.29. Found: C, 74.44; H, 6.38.

EXAMPLE 34

A 2.2 g sample of racemic-3,4-dihydro-7-(phenylmethoxy)-2h-1-benzopyran-2-ol was condensed with (carbethoxymethylene)triphenylphosphorane (3.2 g) using the procedure of Example 30. There was obtained 2.6 g (92.8%) of racemic-3,4-dihydro-7-(phenylmethoxy)-2H-1-benzopyran-2-acetic acid ethyl ester as a yellow oil, after column chromatographic purification. This material was hydrogenolyzed over 0.2 g of 10% palladium on carbon as described in Example 30. There was obtained 1.9 g of racemic-3,4-dihydro-7-hydroxy-2H-1-benzopyran-2-acetic acid ethyl ester as a pale-yellow oil.

EXAMPLE 35

A 0.9 g sample of racemic-3,4-dihydro-7-hydroxy-2H-1-benzopyran-2-acetic acid ethyl ester was alkylated with 3 g of 4'-(3-bromopropoxy)-2'-hydroxy-3'-n-propylacetophenone using the procedure described in Example 31. The crude product (2.6 g) was chromatographed on 50 g of silica gel giving 1.2 g of the desired ester as a pale-yellow oil (eluted with 19:1 toluene-ethyl acetate). This material was saponified with 2.0 g of lithium hydroxide monohydrate using the procedure described in Example 31. The crude acid (1.1 g) was chromatographed on 50 g of silica gel. Elution with 2:1 and 1:1 toluene-ethyl acetate afforded 682 mg (40.5%) of racemic-7-[3-(4-acetyl-3-hydroxy-2-propylphenoxy)-propoxy]-3,4-dihydro-2H-1-benzopyran-2-acetic acid as a pale-yellow solid, mp 107°–109.5° C.

Analysis Calculated for $C_{25}H_{30}O_7$: C, 67.86; H, 6.83. Found: C, 68.07; H, 6.87.

EXAMPLE 36

A solution of 8.75 g of ethyl 6-hydroxychromone-2-carboxylate in 200 ml of acetic acid was hydrogenated in the presence of 2 g of 10% palladium on charcoal at 50 psi and room temperature by shaking the suspension over a period of 17 hours. The catalyst was filtered and the filtrate was evaporated under reduced pressure to give 7.85 g of crude material. Purification of this compound by high-performance liquid chromatography (solvent system, hexane-ethyl acetate 3:1) yielded 4.9 g (59%) of pure crystalline racemic-3,4-dihydro-6-hydroxy-2H-1-benzopyran-2-carboxylic acid ethyl ester. Recrystallization from ethyl-acetate-hexane gave colorless solid, mp 72°–74° C.

Analysis Calculated for $C_{12}H_{14}O_4$: C, 64.85; H, 6.35. Found: C, 64.57; H, 6.45.

EXAMPLE 37

Into a solution of 2.23 g of racemic-ethyl 6-hydroxychroman-2-carboxylate in 30 ml of acetic acid was introduced a stream of boron trifluoride gas at 20°–25° C. A cold water bath was used during the introduction of the gas (30–45 minutes) to control the temperature of the exothermic reaction. The cold bath was removed and the reaction mixture was heated at 80° C. for 5 hours; then the reaction mixture was cooled and carefully poured into a mixture of saturated bicarbonate and ice, and the product was extracted with 1:1 tetrahydrofuran-ether. The crude material obtained after evaporation of the solvent was chromatographed on a silica gel column to yield 1.6 g (60%) of racemic-7-acetyl-6-hydroxy-3,4-dihydro-2H-1-benzopyran-2-carboxylic acid ethyl ester as a viscous oil.

EXAMPLE 38

Using the procedure described in Example 42, 1.0 g of racemic-ethyl 6-hydroxychroman-2-carboxylate was converted into racemic-6-[3-(4-acetyl-3-hydroxy-2-propylphenoxy)propoxy]-3,4-dihydro-2H-1-benzopyran-2-carboxylic acid in 27.3% yield, as a white crystalline material, mp 125°–127° C.

Analysis Calculated for $C_{24}H_{28}O_7$: C, 67.28; H, 6.59. Found: C, 67.27; H, 6.67.

EXAMPLE 39

A mixture of 1.6 g of racemic-7-acetyl-6-hydroxychroman-2-carboxylic acid ethyl ester, 3.0 g of potassium carbonate, 5 ml of 1,3-dibromopropane, 60 ml of dry acetone and 30 ml of dry dimethyl formamide was stirred and refluxed for 20 hours. After removal of most of the solvents in vacuo, the residue was diluted with ether and treated cautiously with 1N hydrochloric acid. The organic phase was separated, washed with saturated sodium bicarbonate solution and water, dried and concentrated in vacuo. The crude bromopropyl derivative (2.1 g) was dissolved in 30 ml of acetone and added to a mixture of 1.2 g of 2′,4′-dihydroxy-3′-propylacetophenone, 2.5 g of anhydrous potassium carbonate, 30 ml of dry acetone and 30 ml of dimethylformamide. The reaction mixture was gently refluxed for 25 hours. After removal of most of the solvent, the product was extracted with ether, the ether extracts washed with brine and dried. The crude material (3.1 g) obtained after evaporation of the solvent was chromatograhed on silica gel to afford 1.3 g (43%) of the desired ester. This material was hydrolyzed by treating the ester (1.3 g) in 18 ml of tetrahydrofuran) with an aqueous solution of lithium hydroxide (2.2 g of lithium hydroxide monohydrate in 18 ml of water). The cloudy reaction mixture was stirred for 21 hours at room temperature, poured into 1N hydrochloric acid and the product extracted with ether. The organic phase was washed with brine, dried and evaporated to give 1.2 g of a viscous yellow oil. Purification by chromatography on a silica gel column afforded 0.778 g (27.3%) of racemic-7-acetyl-6-[3-(4-acetyl-3-hydroxy-2-propylphenoxy)propoxy]-3,4-dihydro-2H-1-benzopyran-2-carboxylic acid as a white crystalline material, mp 140.5°–142.5° C. (from ethyl acetate)

Analysis Calculated for $C_{26}H_{30}O_8$: C, 66.37; H, 6.43. Found: C, 66.44; H, 6.51.

EXAMPLE 40

Using the hydrogenation conditions described in Example 36, 1.09 g of ethyl 7-hydroxychromone-2carboxylate was converted into racemic-ethyl 7-hydroxychroman-2-carboxylate in 53% yield as a crystalline material, mp 81°–82.5° C. (from ethyl acetate-hexane).

Analysis Calculated for $C_{12}H_{14}O_4$0 C, 64.85; H, 6.35. Found: C, 64.60; H, 6.26.

EXAMPLE 41

A 1.1 g sample of racemic ethyl 7-hydroxychroman-2-carboxylate was treated with 10 ml of 1:1 acetic anhydride-pyridine and stirred for 17 hours at room temperature. After removal of the solvents, the residual product (1.2 g) was dissolved in 12 ml of glacial acetic acid and treated with 1.26 ml of borontrifluoride etherate. The reaction mixture was gently refluxed for 17 hours, cooled, poured carefully into a mixture of sodium bicarbonate and ice and the product extracted with 1:1 tetrahydrofuran-ether. After evaporation of the solvent, 1.1 g of crude racemic-7-hydroxy-6-acetylchroman-2-carboxylic acid was obtained. Conversion of this material into the corresponding ethyl ester was achieved by refluxing 1.1 g of the crude acid in absolute ethanol in the presence of 10 mg of p-toluenesulfonic acid for 17 hours. After removal of most of the solvent, the product was extracted with 1:1 tetrahydrofuran-ether, washed with saturated sodium bicarbonate solution, water, dried and the solvents concentrated to give 1.2 g of crude ethyl ester as a mixture of the 6-acetyl and 8-acetyl derivatives in a ratio of about 7:1. This material was purified by column chromatography on silica gel to afford 0.7 g (53.5%) of racemic-6-acetyl-3,4-dihydro-7-hydroxy-2H-1-benzopyran-2-carboxylic acid ethyl ester as a colorless crystalline material mp 93.5°–95.5° C. (from ethyl acetate-hexane).

EXAMPLE 42

A mixture of 1 g of racemic-ethyl 7-hydroxychroman-2-carboxylate, 1.6 g of 4′-(3-bromopropoxy)-2′-hydroxy-3′-propylacetophenone, 1.6 g of anhydrous potassium carbonate, 25 ml of acetone and 12 ml of dimethylformamide was stirred and refluxed for 23 hours. After cooling, 1N hydrochloric acid was cautiously added and the product was extracted with ether. The ether layer was washed with brine, dried, and evaporated in vacuo to afford 3.6 g of an orange oil. Chromatographic purification on silica gel yielded 1.4 g of the alkylated ethy ester. This material, dissolved in 20 ml of tetrahydrofuran, was treated with aqueous lithium hydroxide (2.6 g of lithium hydroxide monohydrate in 20 ml of water) and stirred for 23 hours at room temperature. The reaction mixture was acidified and the product extracted with ether, washed with brine and dried. Solvent removal gave 1.3 g of pale-yellow acid which was purified on a chromatographic column of silica gel to afford 0.554 g (28.7%) of racemic-7-[3-(4-acetyl-3-hydroxy-2-propyl)phenoxy)propoxy]-3,4-dihydro-2H-1-benzopyran-2-carboxylic acid as a white crystalline material mp 142.5°–145° C.

Analysis Calculated for $C_{24}H_{28}O_7$: C, 67.28; H, 6.59. Found: C, 67.34; H, 6.62.

EXAMPLE 43

Using the procedure described in Example 39, 0.840 g of racemic-ethyl 6-acetyl-7-hydroxychroman-2-carboxylate was converted into racemic-6-acetyl-7-[3-(4-acetyl-3-hydroxy-2-propylphenoxy)propoxy]-3,4-dihydro-2H-2-benzopyran-2-carboxylic acid in 49.5% yield as a colorless solid mp 176°–178.5° C. (d) (from ethyl acetate).

Analysis Calculated for $C_{26}H_{30}O_8$: C, 66.37; H, 6.43. Found: C, 66.27; H, 6.39.

EXAMPLE 44

Using the hydrogenation conditions described in Example 36, 5.52 g of ethyl 7-hydroxy-8-propylchromone-2-carboxylate was converted into racemic-ethyl 7-hydroxy-8-propylchroman-2-carboxylate in 43.5% yield, as a viscous pale yellow oil.

EXAMPLE 45

Using the procedure described in Example 41, 1.3 g of racemic-3,4-dihydro-7-hydroxy-8-propyl-2H-1-benzopyran-2-carboxylic acid ethyl ester was converted into the corresponding 6-acetyl derivative in 79.5% yield, as a vicous oil.

EXAMPLE 46

Using the procedure described in Example 42, 1.0 g of racemic-7-hydroxy-8-propylchroman-2-carboxylic acid ethyl ester was converted into racemic-7-[3-(4-acetyl-3-hydroxy-2-propyl)phenoxy)propoxy]-3,4-dihydro-8-propyl-2H-1-benzopyran-2-carboxylic acid as a pale yellow solid, mp 105°–107° C.

Analysis Calculated for $C_{27}H_{34}O_7$: C, 68.92; H, 7.28. Found: C, 69.06; H, 7.29.

EXAMPLE 47

A mixture of 0.85 g of racemic-ethyl 6-acetyl-7-hydroxy-8-propylchroman-2-carboxylate, 1.2 g of anhydrous potassium carbonate, 2.3 ml of 1,3-dibromopropane, 0.1 g of 18-crown-6-ether and 20 ml of acetonitrile was refluxed for 23 hours. After cooling, the reaction mixture was diluted with ether. The organic phase was washed with brine, dried, and evaporated to afford 1.2 g of the bromopropyl derivative as a yellow oil. Using the conditions described in Example 39, this bromide was converted by alkylation of 2',4'-dihydroxy-3'-propylacetophenone and subsequent saponification, into racemic-6-acetyl-7-[3-(4-acetyl-3-hydroxy-2-propylphenoxy)propoxy]-3,4-dihydro-8-propyl-2H-1-benzopyran-2-carboxylic acid in about 40% overall yield. This acid was obtained as a colorless solid, mp 108°–110.5° C. (from ethyl acetate-hexane).

Analysis Calculated for $C_{29}H_{36}O_8$: C, 67.95; H, 7.08. Found: C, 68.16; H, 7.20.

EXAMPLE 48

Using the procedure described in Example 39, with the exception that 1,5-dibromopentane was substituted for 1,3-dibromopropane, racemic-6-acetyl-7-hydroxy-3,4-dihydro-2H-1-benzopyran-2-carboxylic acid ethyl ester was converted into racemic-6-acetyl-7-[5-(4-acetyl-3-hydroxy-2-propylphenoxy)pentyloxy]-3,4-dihydro-2H-1-benzopyran-2-carboxylic acid in 32.8% yield, as a colorless solid, mp 113°–115° C. (from ethyl acetatehexane).

Analysis Calculated for $C_{28}H_{34}O_8$: C, 67.45; H, 6.87. Found: C, 67.61; H, 6.80.

EXAMPLE 49

Using the procedure described in Example 39, with the exception that 1,7-dibromoheptane was substituted for 1,3-dibromopropane, racemic-6-acetyl-7-hydroxy-3,4-dihydro-2H-1-benzopyran-2-carboxylic acid ethyl ester was converted into racemic-6-acetyl-7-[7-(4-acetyl-3-hydroxy-2-propylphenoxy)heptyloxy]-3,4-dihydro-2H-1-benzopyran-2-carboxylic acid as a colorless solid, mp 133°–135° C. (from ethyl acetate-hexane), in 39.1% overall yield.

Analysis Calculated for $C_{30}H_{38}O_8$: C, 68.42; H, 7.27. Found: C, 68.22; H, 7.18.

EXAMPLE 50

Using the procedure described in Example 39, 0.62 g of racemic-8-acetyl-7-hydroxy-3,4-dihydro-2H-1-benzopyran-2-carboxylic acid ethyl ester was converted into racemic-8-acetyl-7[3-(4-acetyl-3-hydroxy-2-propylphenoxy)propoxy]-3,4-dihydro-2H-1-benzopyran-2-carboxylic acid in 27.7% overall yield, as a colorless solid, mp 146.5°–148.5° C. (from ethyl acetate-hexane).

Analysis Calculated for $C_{26}H_{30}O_8$: C, 66.37; H, 6.43. Found: C, 66.51; H, 6.47.

EXAMPLE 51

A 0.125 g sample of racemic-3,4-dihydro-6-hydroxy-2-methyl-2H-1-benzopyran-2-carboxylic acid ethyl ester was converted into racemic-3,4-dihydro-7-acetyl-6-hydroxy-2-methyl-2H-1-benzopyran-2-carboxylic acid ethyl ester in 65.5% yield, as a viscous oil, using the procedure described in Example 37.

EXAMPLE 52

A 96.5 mg sample of racemic-3,4-dihydro-7-acetyl-6-hydroxy-2-methyl-2H-1-benzopyran-2-carboxylic acid ethyl ester was converted into racemic-7-acetyl-6-[3-(4-acetyl-3-hydroxy-2-propylphenoxy)propoxy]-3,4-dihydro-2-methyl-2H-1-benzopyran-2-carboxylic acid in 65.7% yield as a foam, using the procedure described in Example 39.

EXAMPLE 53

A mixture of 1.14 g of 4-benzyloxy-2-hydroxybenzaldehyde, 0.125 g of 1,4-diazabicyclo[2,2,2]octane and 0.65 g of acrylonitrile was stirred and heated at 80°–85° C., under argon, for 2 hours. After removal of the solvent, the residual product was dissolved in tetrahydrofuran-ether(1:1), washed with 1N-sodium hydroxide, water, dried, and the solvents evaporated in vacuo. The crude material (1.10 g) was purified by column chromatography on silica gel to afford 0.6 g (45.7%) of 7-(phenylmethoxy)-2H-1-benzopyran-3-carbonitrile, as a colorless solid mp 95°–98° C. (from ethyl acetatehexane).

Analysis Calculated for $C_{17}H_{13}NO_2$: C, 77.55; H, 4.98; N, 5.32. Found: C, 77.41; H, 5.00; N, 4.80.

EXAMPLE 54

A 2.2 g sample of 7-(phenylmethoxy)-2H-1-benzopyran-3-carbonitrile dissolved in 40 ml of a mixture of tetrahydrofuran-ethyl alcohol (1:1) was treated with 20 ml of a 2N potassium hydroxide and the reaction mixture was refluxed under argon for 21 hours. An additional, 10 ml of 2N potassium hydroxide was added and the mixture was stirred and refluxed for an additional 27 hours. The reaction mixture was acidified with 1N hydrochloric acid, extracted with ethyl acetate, washed with brine, dried and the solvent evaporated in vacuo to afford 2.2 g of an orange solid. This material, dissolved in 30 ml of ethanol containing 0.3 g of p-toluenesulfonic acid monohydrate, was refluxed for 18 hours under argon. after removal of most of the solvent, the residual product was extracted with ether, the extract washed with saturated sodium bicarbonate solution, water, dried and the solvent evaporated to afford 2.3 g of crude ethyl ester. Purification by chromatography on a silica gel column afforded 1.4 g of 7-(phenylmethoxy)-2H-1-benzopyran-3-carboxylic acid ethyl ester as a crystalline material.

EXAMPLE 55

The ester from Example 54 (1.4 g) was dissolved in 25 ml of absolute alcohol and hydrogenated at atmospheric pressure in the presence of 0.2 g of 10% palladium on charcoal. The catalyst was removed by filtration on diatomaceous earth and after removal of the solvent, 0.9 g of racemic-3,4-dihydro-7-hydroxy-2H-1-benzopyran-3-carboxylic acid ethyl ester was obtained as a white solid.

EXAMPLE 56

The ethyl ester from Example 55 was converted into racemic 7-[3-(4-acetyl-3-hydroxy-2-propylphenoxy)-propoxy]-3,4-dihydro-2H-1-benzopyran-3-carboxylic acid in 17.7% overall yield, using the procedures described in Example 42. The acid was obtained as a colorless solid mp 153.5°–155.5° C. (from ethyl acetate-ether-hexane).

Analysis Calculated for $C_{24}H_{28}O_7$: C, 67.28; H, 6.59. Found: C, 67.46; H, 6.66.

EXAMPLE 57

A 0.9 g sample of racemic-7-hydroxy-3,4-dihydro-2H-1-benzopyran-3-carboxylic acid ethyl ester dissolved in 5 ml of pyridine was treated with 1.2 ml of acetic anhydride. After being stirred for 3 hours at room temperature, the reaction mixture was diluted with ether. The organic layer was washed with 2N hydrochloric acid, sodium bicarbonate, brine, dried and the solvent evaporated. There was obtained 1.2 g of crude acetate which was dissolved in 10 ml of glacial acetic acid and treated with 1 ml of boron trifluoride etherate. The reaction mixture was heated at 100° C. under argon for 6 hours. After cooling, ether was added. The organic layer was washed several times with water, dried, and the solvent evaporated in vacuo to afford 1.0 g of an orange oil. The esterification of this material with ethanol was carried out as described in Example 41 giving racemic-6-acetyl-7-hydroxy-3,4-dihydro-2H-1-benzopyran-3-carboxylic acid ethyl ester.

EXAMPLE 58

Racemic-6-acetyl-7-hydroxy-3,4-dihydro-2H-1-benzopyran-3-carboxylic acid ethyl ester was converted into racemic-6-acetyl-7-[3-(4-acetyl-3-hydroxy-2-propylphenoxy)propoxy]-3,4-dihydro-2H-1-benzopyran-3-carboxylic acid using the procedure described in Example 39. The acid product was a colorless solid, mp 127°–129° C. dec. (from ethyl acetate-hexane).

Analysis Calculated for $C_{26}H_{30}O_8$: C, 6.43; H, 6.43. Found: C, 66.45; H. 6.43.

EXAMPLE 59

Using the procedure described in Example 41, 11.3 g of racemic-7-hydroxy-3,4-dihydro-2H-1-benzopyran-2-carboxylic acid ethyl ester was converted into crude racemic-7-hydroxy-6-acetyl-3,4-dihydro-2H-1-benzopyran-2-carboxylic acid in 93% yield (11 g). A 1 g sample of this crude acid was treated with 3.8 g of (−)-(2R,3R)-butanediol in 30 ml of toluene, in the presence of 0.2 g of p-toluenesulfonic acid monohydrate. After 18 hours at reflux, the reaction mixture was cooled and poured into a saturated solution of sodium bicarbonate and the product extracted with ether. The ether extract was washed twice water, dried and concentrated. There was obtained 1.8 g of crude product after removal of the solvents which was a mixture of the 6-acetyl and the 8-acetyl mono-butanediol ester derivatives in a ratio of about 7:1. Purification of this material by HPLC afforded 0.8 g (61%) of [2R,S-2-[(1R*,2R*)]]-6-acetyl-7-hydroxy-3,4-dihydroxy-2H-1-benzopyran-2-carboxylic acid 1-methyl-2-hydroxypropylester, as a viscous pale yellow oil.

EXAMPLE 60

Using the procedure described in Example 25, 3.5 g of [2R,S-2-[(1R*,2R*)]]-6-acetyl-7-hydroxy-3,4-dihydro-2H-1-benzopyran-2-carboxylic acid 1-methyl-2-hydroxypropyl ester, 12 ml of 1,5-dibromopentane, 7.2. g of anhydrous potassium carbonate in 100 ml acetone and 50 ml of N,N-dimethylformamide afforded 2.6 g (50%) of [2R,S-2-[(1R*,2R*)]]-6-acetyl-7-[(5-bromopentyl)oxy]-3,4-dihydro-2H-1-benzopyran-2-carboxylic acid 2-hydroxy-1-methylpropyl ester. This material was then separated by HPLC (toluene-ethylacetate 2:1) with recyling. The less polar diastereoisomer was recrystallized from ethyl ether giving 786 mg of [2S-[2beta(1R*,2R*)]]-6-acetyl-7-[(5-bromopentyl)oxy]-3,4-dihydro-2H-1-benzopyran-2-carboxylic acid 2-hydroxy-1-methylpropyl ester, as a colorless solid, mp 94.5°–98° C.; $[\alpha]D^{25} -7.99°$ (Cl, CHCl$_3$).

Analysis for $C_{21}H_{29}BrO_6$: Calculated: C, 55.15; H, 6.39, Found: C, 54.79; H, 6.20.

Recrystallization of the more polar diastereoisomer from ethyl ether gave 1.03 g of [2R-[2alpha(1R*,2R*)]]-6-acetyl-7-[(5-bromopentyl)oxy]-3,4-dihydro-2H-1-benzopyran-2-carboxylic acid 2-hydroxy-1-methylpropyl ester (mp 80°–83° C.; $[\alpha]D^{25} -21.49°$ (c1, CHCl$_3$)) as a colorless solid.

Analysis for $C_{21}H_{29}BrO_6$: Calculated: C, 55.15; H, 6.39. Found: C, 55.06; H, 6.39.

EXAMPLE 61

Using the procedure described in Example 26, 199.8 mg of [2S-(2beta(1R*,2R*)]]-6-acetyl-7-[(5-bromopentyl)oxy]-3,4-dihydro-2H-1-benzopyran-2-carboxylic acid 2-hydroxy-1-methylpropyl ester was alkylated with 2′,4′-dihydroxy-3′-n-propylacetophenone. After chromatographic purification on a silica gel column, 106 mg (42.8%) of [2S-(2beta(1R*,2R*)]]-6-acetyl-7-[5-(4-acetyl-3-hydroxy-2-propylphenoxy)pentyloxy]-3,4-dihydro-2H-1-benzopyran-2-carboxylic acid 2-hydroxy-1-methyl propyl ester was obtained $[\alpha]D^{25} -7.25°$ (c1, CHCl$_3$); (mp 124°–127.5° C.) (recrystallized from ethyl acetate-hexane).

Analysis for $C_{32}H_{42}O_9$: Calculated: C, 67.35; H, 7.42. Found: C, 67.14; H, 7.51.

EXAMPLE 62

Using the procedure of example 61, 554 mg of the 2R-bromo ester from example 60 was converted into [2R-(2alpha(1R*,2R*)]-6-acetyl-7-[5-(4-acetyl-3-hydroxy-2-propylphenoxy)pentyloxy]-3,4-dihydro-2H-1-benzopyran-2-carboxylic acid 2-hydroxy-1-methylpropyl ester in 72.6% yield (mp 100°–105° C.; $[\alpha]D^{25} -15.75°$ (c1, CHCl$_3$); from ethyl acetate-hexane).

Analysis for $C_{32}H_{42}O_9$: Calculated: C, 67.25; H, 7.42. Found: C, 66.98; H, 7.39.

EXAMPLE 63

A 405 mg sample of the 2S-isomeric ester from example 61 was saponified with lithium hydroxide monohydrate (0.6 g) in 10 ml of 1:1 tetrahydrofuran-water using the procedure described in Example 4. After crystallization from ethyl acetate-hexane, 185 mg (52.2%) of (S)-6-acetyl-7-[5-(4-acetyl-3-hydroxy-2-propylphenoxy)pentyloxy]-3,4-dihydro-2H-1-benzopyran-2-carboxylic acid, mp 94°–97.5° C. $[\alpha]D^{25} +1.25°$ (c1, CHCl$_3$) was obtained.

Analysis for $C_{28}H_{34}O_8$: Calculated: C, 67.45; H, 6.87. Found: C, 66.60; H, 6.70.

EXAMPLE 64

Using the procedure of example 63, 502 mg of the 2R-isomeric ester from example 62 yielded, after crystallization from ethyl acetate hexane, 185 mg (40.7%) of (R)-6-acetyl-7-[5-(4-acetyl-3-hydroxy-2-propylphenoxy)pentyloxy]-3,4-dihydro-2H-1-benzopyran-2-carboxylic acid, mp 102.5°–108° C., $[\alpha]D^{25} -1.02°$ (c1, CHCl$_3$).

Analysis for $C_{28}H_{34}O_8$: Calculated: C, 67.45; H, 6.87. Found: C, 67.26; H, 6.78.

EXAMPLE 65

A mixture of 1 g (4.5 mmoles) of racemic-3,4-dihydro-7-hydroxy-2H-1-benzopyran-2-carboxylic acid ethyl ester, 3.7 ml (27.2 mmoles) of 1,5-dibromopentane, 2 g (14.5 mmoles) of anhydrous potassium carbonate, 30 ml of acetone, and 15 ml of N,N-dimethylformamide was stirred and refluxed for 20 hours. The mixture was cooled and diluted with ether. The ether solution was washed with water and saturated brine, dried over anhydrous magnesium sulfate, filtered and concentrated under reduced pressure giving 7.2 g of a yellow liquid. This material was chromatographed on 50 g of silica gel. Elution with 19:1 and 9:1 toluene-ethyl acetate afforded 1.2 g (72%) of racemic-7-[(5-bromopentyl)oxy]-3,4-dihydro-2H-1-benzopyran-2-carboxylic acid ethyl ester as a pale yellow oil.

EXAMPLE 66

Using the procedure and molar proportions of example 65, the following compounds were prepared from the indicated starting materials. All compounds were purified by chromatography on silica gel and were isolated as pale yellow oils:

Racemic-6-acetyl-7-[(5-bromopentyl)oxy]-3,4-dihydro-8-propyl-2H-1-benzopyran-2-carboxylic acid ethyl ester from racemic-6-acetyl-7-hydroxy-3,4-dihydro-8-propyl-2H-1-benzopyran-2-carboxylic acid ethyl ester and 1,5-dibromopentane.

Racemic-6-acetyl-7-[(5-bromopentyl)oxy]-3,4-dihydro-2H-1-benzopyran-2-carboxylic acid ethyl ester from racemic-6-acetyl-3,4-dihydro-7-hydroxy-2H-1-benzopyran-2-carboxylic acid ethyl ester and 1,5-dibromohexane.

Racemic-6-acetyl-7-[(6-bromohexyl)oxy]-3,4-dihydro-2H-1-benzopyran-2-carboxylic acid ethyl ester from racemic-6-acetyl-3,4-dihydro-7-hydroxy-2H-1-benzopyran-2-carboxylic acid ethyl ester and 1,6-dibromopentane.

Racemic-6-acetyl-7-[(4-bromobutyl)oxy]-3,4-dihydro-2H-1-benzopyran-2-carboxylic acid ethyl ester from racemic-6-acetyl-3,4-dihydro-7-hydroxy-2H-1-benzopyran-2-carboxylic acid ethyl ester and 1,4-dibromobutane.

Racemic-7-[(5-bromopentyl)oxy]-3,4-dihydro-8-propyl-2H-1-benzopyran-2-carboxylic acid ethyl ester from racemic-3,4-dihydro-7-hydroxy-8-propyl-2H-1-benzopyran-2-carboxylic acid ethyl ester and 1,5-dibromopentane.

Racemic-8-acetyl-7-[(5-bromopentyl)oxy]-3,4-dihydro-2H-1-benzopyran-2-carboxylic acid methyl ester from racmic-8-acetyl-3,4-dihydro-7-hydroxy-2H-1-benzopyran-2-carboxylic acid methyl ester and 1,5-dibromopentane.

EXAMPLE 67

A mixture of 1.2 g (3.23 mmoles) of racemic-7-[(5-bromopentyl)oxy]-3,4-dihydro-2H-1-benzopyran-2-carboxylic acid ethyl ester, 1.0 g (5.15 mmoles) of 2',4'-dihydroxy-3'-propylacetophenone, 1.8 g (13.0 mmoles) of anhydrous potassium carbonate, 30 ml of acetone, and 15 ml of N,N-dimethylformamide was stirred and refluxed for 6 hr. After being cooled, the mixture was diluted with ether. The ether phase was washed with water and brine, dried over anhydrous magnesium sulfate, filtered and concentrated under reduced pressure. The residue (2.1 g) was chromatographed on 50 g of silica gel. Elution with 19:1 toluene-ethyl acetate afforded 1.3 g (83%) of racemic-7-[5-(4-acetyl-3-hydroxy-2-propylphenoxy)pentyloxy]-3,4-dihydro-2H-1-benzopyran-2-carboxylic acid ethyl ester as a yellow oil.

EXAMPLE 68

Using the procedure and molar proportions of example 67, the following compounds were prepared from the indicated starting materials. All compounds were purified by chromatography on silica gel and were isolated as pale yellow oils:

Rac-6-acetyl-7-[5-(4-acetyl-3-hydroxyphenoxy)pentyloxy]-3,4-dihydro-8-propyl-2H-1-benzopyran-2-carboxylic acid ethyl ester from racemic-6-acetyl-7-[(5-bromopentyl)oxy]-3,4-dihydro-8-propyl-2H-1-benzopyran-2-carboxylic acid ethyl ester and 2',4'-dihydroxyacetophenone.

Rac-6-acetyl-7-[5-(4-acetyl-3-hydroxyphenoxy)pentyloxy]-3,4-dihydro-2H-1-benzopyran-2-carboxylic acid ethyl ester from racemic-6-acetyl-7-[(5-bromopentyl)oxy]-3,4-dihydro-2H-1-benzopyran-2-carboxylic acid ethyl ester and 2',4'-dihydroxyacetophenone.

Rac-6-acetyl-7-[5-(4-acetyl-3-hydroxy-2-propylphenoxy)pentyloxy]-3,4-dihydro-8-propyl-2H-1-benzopyran-2-carboxylic acid ethyl ester from racemic-6-acetyl-7-[(5-bromopentyl)oxy]-3,4-dihydro-8-propyl-2H-1-benzopyran-2-carboxylic acid ethyl ester and 2',4'-dihydroxy-3'-propylacetophenone.

Rac-7-[5-(4-Acetyl-3-hydroxyphenoxy)pentyloxy]-3,4-dihydro-2H-1-benzopyran-2-carboxylic acid ethyl ester from racemic-7-[(5-bromopentyl)oxy]-3,4-dihydro-2H-1-benzopyran-2-carboxylic acid ethyl ester and 2',4'-dihydroxyacetophenone.

Rac-6-acetyl-7-[6-(4-acetyl-3-hydroxy-2-propylphenoxy)hexyloxy]-3,4-dihydro-2H-1-benzopyran-2-carboxylic acid ethyl ester from racemic-6-acetyl-7-[(6-bromohexyl)oxy]-3,4-dihydro-2H-1-benzoyran-2-carboxylic acid ethyl ester and 2',4'-dihydroxy-3'-propylacetophenone.

Rac-6-acetyl-7-[4-(4-acetyl-3-hydroxy-2-propylphenoxy)butoxy]-3,4-dihydro-2H-1-benzopyran-2-carboxylic acid ethyl ester from racemic-6-acetyl-7-[(4-bromobutyl)oxy]-3,4-dihydro-2H-1-benzopyran-2-carboxylic acid ethyl ester and 2',4'-dihydroxy-3'-propylacetophenone.

Rac-7-[5-(4-acetyl-3-hydroxyphenoxy)pentyloxy]-3,4-dihydro-8-propyl-2H-1-benzopyran-2-carboxylic acid ethyl ester from racemic-7-[(5-bromopentyl)oxy]-3,4-dihydro-8-propyl-2H-1-benzopyran-2-carboxylic acid ethyl ester and 2',4'-dihydroxyacetophenone.

Rac-7-[5-(4-acetyl-3-hydroxy-2-propylphenoxy)pentyloxy]-3,4-dihydroxy-8-propyl-2H-1-benzopyran-2-carboxylic acid ethyl ester from racemic-7-[(5-bromopentyl)oxy]-3,4-dihydro-8-propyl-2H-1-benzopyran-2-carboxylic acid ethyl ester and 2',4'-dihydroxy-3'-propylacetophenone.

Rac-8-acetyl-7-[[5-(4-acetyl-3-hydroxy-2-propylphenoxy)pentyloxy]-3,4-dihydro-2H-1-benzopyran-2-carboxylic acid methyl ester from racemic-8-acetyl-7-[(5-bromopentyl)oxy]-3,4-dihydro-2H-1-benzopyran-2-carboxylic acid methyl ester and 2',4'-dihydroxy-3'-propylacetophenone.

EXAMPLE 69

A mixture of 1.3 g (2.68 mmoles) of the ester product from example 67, 60 ml of 1:1 tetrahydrofuran-water, and 2.4 g (57.1 mmoles) of lithium hydroxide monohydrate was stirred at room temperature for 5 hours. The mixture was diluted with water and extracted three times with ether. The aqueous phase was acidified to pH 1 with 2N HCl and extracted three times with ethyl acetate. The ethyl acetate extracts were combined, washed with saturated brine, dried over anhydrous magnesium sulfate, filtered and concentrated under reduced pressure. The residue was recrystallized from ethyl acetate giving 0.725 g (59%) of racemic-7-[5-(4-acetyl-3-hydroxy-2-propylphenoxy)pentyloxy]-3,4-dihydro-2H-1-benzopyran-2-carboxylic acid as a colorless solid, mp 124°–126.5° C.

Analysis Calculated for $C_{26}H_{32}O_7$: C, 68.40; H, 7.07. Found C, 68.34; H, 7.29.

Using the procedure and molar proportions of example 69, the acids shown in the following table were prepared by saponification of the corresponding ester from example 68:

ramethyl-2H-1-benzopyran-2-carboxylic acid methyl ester, $[\alpha]D^{25} -34.60°$ (c2, $CHCl_3$), in 88.5% yield.

Analysis Calculated for $C_{20}H_{29}BrO_4$: C, 58.12; H, 7.07; Br 19.33. Found: C, 58.00; H, 7.19; Br, 19.33.

EXAMPLE 73

Using the procedure and molar proportions of example 71, 1 g of racemic-6-hydroxy-3,4-dihydro-2,5,7,8-tetramethyl-2H-1-benzopyran-2-carboxylic acid methyl ester was alkylated with 1,5-dibromopentane giving

| Microanalysis | Recryst. mp °C. | Recryst. from | Formula | Calc % C.H | Found % C.H |
|---|---|---|---|---|---|
| rac-6-acetyl-7-[5-(4-acetyl-3-hydroxyphenoxy)pentyloxy]-3,4-dihydro-8-propyl-2H—1-benzopyran-2-carboxylic acid | 105–107 | Ethyl Acetate-Hexane | $C_{28}H_{34}O_8$ | 67.45,6.87 | 67.24,6.91 |
| rac-6-acetyl-7-[5-(4-acetyl-3-hydroxyphenoxy)pentyloxy]-3,4-dihydro-2H—1-benzopyran-2-carboxylic acid | 183–185.5 | Ethyl Acetate | $C_{25}H_{28}O_8$ | 65.78,6.18 | 65.80,6.08 |
| rac-6-acetyl-7-[5-(4-acetyl-3-hydroxy-2-propylphenoxy)-pentyloxy]-3,4-dihydro-8-propyl-2H—1-benzopyran-2-carboxylic acid | oil | — | $C_{31}H_{40}O_8$ | 68.87,7.46 | 68.76,7.70 |
| rac-7-[5-(4-acetyl-3-hydroxyphenoxy)pentyloxy]-3,4-dihydro-2H—1-benzopyran-2-carboxylic acid | 146.5–149 | Ethyl Acetate-Hexane | $C_{23}H_{26}O_7$ | 66.65,6.32 | 66.51,6.29 |
| rac-6-acetyl-7-[6-(4-acetyl-3-hydroxy-2-propyl-phenoxy)hexyloxy]-3,4-dihydro-2H—1-benzopyran-2-carboxylic acid | 138.5–142 | Ethyl Acetate-Hexane | $C_{29}H_{36}O_8$ | 67.95,7.08 | 67.99,7.14 |
| rac-6-acetyl-7-[4-(4-acetyl-3-hydroxy-2-propyl-phenoxy)butoxy]-3,4-dihydro-2H—1-benzopyran-2-carboxylic acid | 137–140 | Ethyl Acetate-Hexane | $C_{27}H_{32}O_8$ | 66.93,6.66 | 67.21,6.77 |
| rac-7-[5-(4-acetyl-3-hydroxyphenoxy)pentyloxy]-3,4-dihydro-8-propyl-2H—1-benzopyran-2-carboxylic acid | 120–123 | Ethyl Acetate-Hexane | $C_{26}H_{32}O_7$ | 68.40,7.07 | 68.70,7.14 |
| rac-7-[5-(4-acetyl-3-hydroxy-2-propylphenoxy)pentyl-oxy]-3,4-dihydro-8-propyl-2H—1-benzopyran-2-carboxylic acid | oil | — | $C_{29}H_{38}O_7$ | 69.86,7.68 | 70.02,7.80 |
| rac-8-acetyl-7-[[5-(4-acetyl-3-hydroxy-2-propylphenoxy)-pentyl]oxy]-3,4dihydro-2H—1-benzopyran-2-carboxylic acid | 134–136 | Acetonitrile | $C_{28}H_{34}O_8$ | 67.45,6.87 | 67.20,6.84 |

EXAMPLE 71

A mixture of 6.5 g (24.6 mmoles) of (R)-(+)-6-hydroxy-3,4-dihydro-2,5,7,8-tetramethyl-2H-1-benzopyran-2-carboxylic acid methyl ester, 10.37 g (75.1 mmoles) of anhydrous potassium carbonate, 1.12 g of 18-crown-6, 39.3 ml (0.2 mole) of 1,5-dibromopentane, and 150 ml of acetonitrile was stirred and refluxed for 21 hours. After being cooled, the mixture was treated with ether and water. The organic layer was separated, washed with water and brine, dried over anhydrous magnesium sulfate, filtered and concentrated under reduced pressure. The residue (68 g) was purified first by column chromatography on silica gel (400 g; eluting with 49:1 toluene-ethyl acetate) and then by preparative HPLC on silica gel using 9:1 hexane-ethyl acetate as the mobile phase. There was obtained 9.71 g (95.6%) of (R)-(+)-6-[(5-bromopentyl)oxy]-3,4-dihydro-2,5,7,8-tetramethyl-2H-1-benzopyran-2-carboxylic acid methyl ester as a solid. Recrystallization from ethanol gave a colorless solid mp 64°–65.5° C., $[\alpha]D^{25} +36.37°$ (c2, $CHCl_3$).

Analysis Calculated for $C_{20}H_{29}BrO_4$: C, 58.12; H, 7.07; Br, 19.33. Found: C, 58.01; H, 7.07; Br, 19.20.

EXAMPLE 72

Using the procedure and molar proportions of example 71, (S)-(−)-6-hydroxy-3,4-dihydro-2,5,7,8-tetramethyl-2H-1-benzopyran-2-carboxylic acid methyl ester was alkylated with 1,5-dibromopentane giving (S)-(−)-6-[(5-bromopentyl)oxy]-3,4-dihydro-2,5,7,8-tet- racemic-6-[(5-bromopentyl)-oxy]-3,4-dihydro-2,5,7,8-tetramethyl-2H-1-benzopyran-2-carboxylic acid methyl ester as a colorless solid, mp 72.5°–74.5° C. in 90% yield after purification by chromatography on silica gel.

Analysis Calculated for $C_{20}H_{29}BrO_4$: C, 58.12; H, 7.07; Br, 19.33. Found: C, 58.13; H, 7.15; Br, 19.30.

EXAMPLE 74

A mixture of 7.35 g (17.8 mmoles) of the (R)-(+)-bromo ester product from example 71, 3.85 g (19.8 mmoles) of 2′,4′-dihydroxy-3′-propylacetophenone, 8.93 g (64.7 mmoles) of anhydrous potassium carbonates, 154 ml of dry acetone, and 77 ml of dry N,N-dimethylformamide was stirred and refluxed for 5.5 hr. The mixture was cooled and diluted with ethyl acetate. The organic phase was washed with water and saturated brine, dried over anhydrous magnesium sulfate, filtered and concentrated under reduced pressure giving 10.8 g of an oil. This material was purified by preparative HPLC on silica gel using 2:1 hexane-ethyl acetate as the mobile phase. There was obtained 9.1 g (97%) of (R)-(+)-6-[5-(4-acetyl-3-hydroxy-2-propylphenoxy)-pentyloxy]-3,4-dihydro-2,5,7,8-tetramethyl-2H-1-benzopyran-2-carboxylic acid methyl ester as a yellow oil, $[\alpha]D^{25} +26.62°$ (c2, $CHCl_3$).

Analysis Calculated for $C_{31}H_{42}O_7$: C, 70.70; H, 8.04. Found: C, 70.06; H, 8.18.

EXAMPLE 75

Using the procedure of example 74, the (S)-(−)-bromo ester product from example 72 (8.4 g) was converted by alkylation of 2′,4′-dihydroxy-3′- propylacetophenone (4.4 g) into (S)-(−)-6-[5-(4-acetyl-3-hydroxy-2-propylphenoxy)-pentyloxy]-3,4-dihydro-2,5,7,8-tetramethyl-2H-1-benzopyran-2-carboxylic acid methyl ester in 91% yield. This material was a yellow oil.

Analysis Calculated for $C_{31}H_{42}O_7$: C, 70.70; H, 8.04. Found: C, 70.13; H, 7.73.

EXAMPLE 76

Using the procedure and molar proportions described in example 74, 1.2 g of the racemic bromo ester product from example 73 was converted by alkylation of 2',4'-dihydroxy-3'-propylacetophenone (0.834 g) into racemic 6-[5-(4-acetyl-3-hydroxy-2-propylphenoxy)pentyloxy]-3,4-dihydro-2,5,7,8-tetramethyl-2H-1-benzopyran-2-carboxylic acid methyl ester in 72% yield, as a pale yellow oil.

Analysis Calculated for $C_{31}H_{42}O_7$: C, 70.70; H, 8.04; Found: C, 70.44; H, 7.97.

EXAMPLE 77

A mixture of 7.55 g (14.3 mmoles) of the (R)-(+)-ester product from example 74, 140 ml of tetrahydrofuran, 90 ml of water, and 12.6 g (0.21 mole) of lithium hydroxide monohydrate was stirred for 7 hours at room temperature and kept at 0° C. for 17 hr. The mixture was poured into cold 3N HCl. The organic materials were extracted three times with ethyl acetate. The extracts were combined, washed with water and saturated brine, dried over anhydrous magnesium sulfate, filtered and concentrated under reduced pressure. The residual yellow glass (7.3 g) was chromatographed on 350 g of silica gel. Elution with 4:1, 2:1, and 1:1 toluene-ethyl acetate gave the desired acid (5 g) which was recrystallized from acetonitrile. There was obtained 2.49 g (34%) of (R)-(+)-6-[5-(4-acetyl-3-hydroxy-2-propylphenoxy)pentyloxy]-3,4-dihydro-2,5,7,8-tetramethyl-2H-1-benzopyran-2-carboxylic acid as a colorless solid, mp 92.5°–95° C., $[\alpha]D^{25}$ +37.86° (c2, CHCl$_3$).

Analysis Calculated for $C_{30}H_{40}O_7$: C, 70.29; H, 7.87. Found: C, 70.25; H, 7.92.

EXAMPLE 78

Using the procedure of example 77, 9.35 g (17.8 mmoles) of the (S)-(−)-ester product from example 75 was saponified. (S)-(−)-6-[5-(4-acetyl-3-hydroxy-2-propylphenoxy)pentyloxy]-3,4-dihydro-2,5,7,8-tetramethyl-2H-1-benzopyran-2-carboxylic acid was obtained as a colorless solid, mp 90°–93.5° C. $[\alpha]D^{25}$ −38.18° (c2, CHCl$_3$), after recrystallization from acetonitrile.

Analysis Calculated for $C_{30}H_{40}O_7$: C, 70.29; H, 7.87. Found: C, 70.50; H, 8.11.

EXAMPLE 79

Using the procedure of example 77, 5.8 g (11 mmoles) of the racemic ester from example 76 was saponified. There was obtained 2.77 g (49%) of racemic-6-[5-(4-acetyl-3-hydroxy-2-propylphenoxy)pentyloxy]-3,4-dihydro-2,5,7,8-tetramethyl-2H-1-benzopyran-2-carboxylic acid as a colorless solid, mp 92.5°–95° C.

Analysis Calculated for $C_{30}H_{40}O_7$: C, 70.29; H, 7.87. Found: C, 70,28; H, 7.98.

EXAMPLE 80

A mixture of 2 g (4 mmoles) of racemic-6-acetyl-7-[5-(4-acetyl-3-hydroxy-2-propylphenoxy)pentyloxy]-3,4-dihydro-2H-1-benzopyran-2-carboxylic acid and 155 ml of water was treated with 40 ml (4 mmoles) of 0.1N aqueous sodium hydroxide solution. The mixture was stirred for 2 hours at room temperature then filtered with suction. The filtrate was freeze-dried giving a solid residue which was dissolved in hot ethyl acetate containing a small amount of ethanol. Hexane was added and a precipitate resulted. The mixture was stored at 0° C. overnight then filtered with suction. The solid was washed with ethyl acetate-hexane (2:1) and the recrystallization procedure was repeated. After drying under high vacuum at 60° C., there was obtained 1.6 g (77%) of the monosodium salt of the starting acid as a colorless solid.

Analysis Calculated for $C_{28}H_{33}NaO_8$: C, 64.61; H, 6.39; Na, 4.42. Found: C, 64.50; H, 6.55; Na, 4.17.

EXAMPLE 81

To a solution of 2 g (4 mmoles) of racemic-6-acetyl-7-[5-(4-acetyl-3-hydroxy-2-propylphenoxy)pentyloxy]-3,4-dihydro-2H-1-benzopyran-2-carboxylic acid in 15 ml of ethanol was added a solution of 0.242 g (2 mmoles) of d-(+)-α-methylbenzylamine in 4 ml of ether. The resulting solution was diluted with 10 ml of ether and stored at 0° C. The precipitate was filtered with suction and washed with ether. Recrystallization from ethanol gave 0.742 g (60%) of a colorless solid, mp 167°–170° C. which was mainly the d-amine salt of the (S)-acid. This salt was suspended in ethyl acetate and shaken with 1N HCl. The organic layer was separated, washed with water, dried over anhydrous magnesium sulfate, filtered, and concentrated under reduced pressure. There was obtained 0.58 g of (S)-6-acetyl-7-[5-(4-acetyl-3-hydroxy-2-propylphenoxy)pentyloxy]-3,4-dihydro-2H-1-benzopyran-2-carboxylic acid as a solid. A sample of this material was esterified with diazomethane. The resulting methyl ester was analyzed for enantiomeric composition by liquid chromatography on a 30 cm Pirkle covalent phenylglycine column. This analysis revealed that the acid obtained by this resolution procedure was composed of 95.3% of the (S)-enantiomer (less polar methyl ester) and 4.7% of the (R)-enantiomer (more polar methyl ester).

EXAMPLE 82

A mixture of 6 g (27 mmoles) of racemic-3,4-dihydro-7-hydroxy-2H-1-benzopyran-2-carboxylic acid ethyl ester, 6.8 g (54 mmoles) of benzyl chloride, 7.5 g (54 mmoles) of anhydrous potassium carbonate, and 4.5 g (27 mmoles) of potassium iodide in 100 ml of acetone was stirred and refluxed for 7 hr. Most of the acetone was removed under reduced pressure and the residue was diluted with ethyl acetate. The organic phase was washed with water, dried over anhydrous magnesium sulfate, filtered and concentrated under reduced pressure giving 17.4 g of a yellow oil. This material was chromatographed on silica gel. Elution with 19:1 toluene-ethyl acetate afforded 6.9 g (78%) of racemic-3,4-dihydro-7-(phenylmethoxy)-2H-1-benzopyran-2-carboxylic acid ethyl ester as a yellow oil.

EXAMPLE 83

The ether ester product from example 82 (6.9 g, 22 mmoles) was dissolved in 70 ml of toluene and the solution was cooled to −78° C. (dry-ice-acetone bath). With stirring, 15.6 ml of a 25% solution of diisobutylaluminum hydride in toluene was added dropwise. The reaction mixture was stirred at −78° C. for 2 hours whereupon 2.5 ml of methanol was cautiously added followed by 2N HCl and ice. The mixture was extracted with ethyl acetate and the organic extracts were combined, washed with saturated brine, dried over anhydrous magnesium sulfate, filtered, and concentrated under reduced pressure. The residue (7.6 g) was chromatographed on silica gel. Elution with 9:1 toluene-ethyl acetate gave 5.6 g (70%) of racemic-3,4-dihydro-7-(phenylmethoxy)-2H-1-benzopyran-2-carboxaldehyde as a pale yellow oil.

EXAMPLE 84

Using the procedure of example 30, 2.7 g (10 mmoles) of the aldehyde product from example 83 was condensed with 3.7 g (10.6 mmoles) of (carbethoxymethylene)triphenylphosphorane, in 30 ml of toluene (1.5 hours at 100° C.). After chromatography of the crude product on 50 g of silica gel (eluting with toluene), there was obtained 3.0 g (88.8%) of racemic-3,4-dihydro-7-(phenylmethoxy)-2H-1-benzopyran-2-propenoic acid ethyl ester (mixture of E- and Z-isomers), as a pale-yellow oil.

EXAMPLE 85

The propenoic ester product from example 84 (3 g; 8.9 mmoles) was hydrogenated at atmospheric pressure and room temperature, over 0.3 g of 10% palladium on carbon, in ethyl acetate (35 ml), giving 2.4 g of racemic-3,4-dihydro-7-hydroxy-2H-1-propanoic acid ethyl ester as a viscous oil, after filtration of the catalyst and solvent evaporation.

EXAMPLE 86

Using the procedure of example 41, the propanoic ester product from example 85 was converted into 1.4 g (54%) of racemic-6-acetyl-3,4-dihydro-7-hydroxy-2H-1-benzopyran-2-propanoic acid ethyl ester, a yellow oil which crystallized on standing, obtained after chromatography on silica gel (eluting with 19:1 toluene-ethyl acetate).

EXAMPLE 87

Using the procedure of example 65, the acetyl propanoic ester product from example 86 (1.4 g, 4.79 mmoles) was converted into racemic-6-acetyl-7-[(5-bromopentyl)oxy]-3,4-dihydro-2H-1-benzopyran-2-propanoic acid ethyl ester in 76% yield (1.6 g) as a yellow oil which crystallized on standing (purified by chromatography on silica gel, eluting with 19:1 toluene-ethyl acetate).

EXAMPLE 88

Using the procedure of example 67, the bromoester product from example 87 (1.6 g; 3.63 mmoles) was converted into racemic-6-acetyl-7-[(5-(4-acetyl-3-hydroxy-2-propylphenoxy)pentyloxy]-3,4-dihydro-2H-1-benzopyran-2-propanoic acid ethyl ester by alkylation of 2',4'-dihydroxy-3'-propylacetophenone. After purification by chromatography on silica gel (eluting with 9:1 and 4:1 toluene-ethyl acetate), the ester product was obtained in 79% yield (1.6 g) as a pale-yellow oil.

EXAMPLE 89

Using the procedure of example 69, the ester product from example 88 (1.6 g; 2.89 mmoles) was saponified giving 1 g (66%) of racemic-6-acetyl-7-[5-(4-acetyl-3-hydroxy-2-propylphenoxy)pentyloxy]-3,4-dihydro-2H-1-benzopyran-2-propanoic acid as a colorless solid mp 126.5°–129° C. after recrystallization from ethyl acetate-hexane and then acetonitrile.

Analysis Calculated for $C_{30}H_{38}O_8$: C, 68.42; H, 7.27. Found: C, 68.42; H, 7.49.

EXAMPLE 90

Using the procedure of example 30, 2.7 g (10 mmoles) of the aldehyde product from example 83 was condensed with 4.4 g (12 mmoles) of ethyl 4(triphenylphosphoranylidene)-2-butenoate in 30 ml of toluene (3.5 hr at 100° C.). Chromatography of the crude product of 100 g of silica gel gave 1.1 g (30%) of racemic-5-[3,4-dihydro-7-(phenylmethoxy)-2H-1-benzopyran-2-yl]-2,4-pentadienoic acid ethyl ester (mixture of E- and Z-isomers) as a yellow oil eluted with toluene and 19:1 toluene-ethyl acetate.

EXAMPLE 91

The dienoic ester product from example 90 (1.1 g; 3.02 mmoles) was hydrogenated at atmospheric pressure and room temperature, in 15 ml of ethyl acetate, over 0.95 g of 10% palladium on carbon. The catalyst was filtered and the filtrate was concentrated under reduced pressure giving 0.9 g (100%) of racemic-3,4-dihydro-7-hydroxy-2H-1-benzopyran-2-pentanoic acid ethyl ester as a pale-yellow oil.

EXAMPLE 92

Using the procedure of example 41, the pentanoic ester product from example 91 was converted into racemic-6-acetyl-3,4-dihydro-7-hydroxy-2H-1-benzopyran-2-pentanoic acid ethyl ester (0.4 g; 41%) as a yellow oil which crystallized on standing.

EXAMPLE 93

Using the procedure of example 65, the acetyl pentanoic ester from example 92 (0.4 g; 1.25 mmoles) was converted into racemic-6-acetyl-7-[(5-bromopentyl)oxy]-3,4-dihydro-2H-1-benzopyran-2-pentanoic acid ethyl ester as a yelow oil obtained in 51% yield (0.3 g) after column chromatography on silica gel (eluting with 19:1 toluene-ethyl acetate).

EXAMPLE 94

Using the procedure of example 67, the bromo ester product from example 93 (0.3 g; 0.64 mmole) was converted into racemic-6-acetyl-7-[5-(4-acetyl-3-hydroxy-2-propylphenoxy)pentyloxy]-3,4-dihydro-2H-1-benzopyran-2-pentanoic acid ethyl ester by alkylation of 2',4'-dihydroxy-3'-propylacetophenone. After purification by chromatography on silica gel (eluting with 19:1 toluene-ethyl acetate), the ester product was obtained in 80% yield (0.3 g) as a yellow oil.

EXAMPLE 95

Using the procedure of example 69, the ester product from example 94 (0.3 g, 0.51 mmoles) was saponified giving 0.137 g (48%) of racemic-6-acetyl-7-[5-(4-acetyl-3-hydroxy-2-propylphenoxy)pentyloxy]-3,4-dihydro-2H-1-benzopyran-2-pentanoic acid as a colorless solid, mp 116°–120.5° C., after recrystallization from acetonitrile.

Analysis Calculated for $C_{32}H_{42}O_8$: C, 69.29; H, 7.63. Found: C, 69.35; H, 7.66.

EXAMPLE 96

Aerosol Formulation (Freon Suspension Aerosol)

| Ingredients | mg/100 μl | | |
|---|---|---|---|
| | 1 mg | 10 mg | 25 mg |
| racemic-6-acetyl-7-[5-(4-acetyl-3-hydroxy-2-propylphenoxy)-pentyloxy]-3,4-dihydro-2H—1-benzopyran-2-carboxylic acid (micronized) | 1 mg | 10 mg | 25 mg |
| Glyceryl Trioleate | 0.03 mg | 3.0 mg | 7.5 mg |
| Freon 114* 30 parts } To Make | 100 μl | 100 μl | 100 μl |
| Freon 12 70 parts | | | |

*Freon 11 can be substituted.

Procedure:

Micronize racemic-6-acetyl-7-[5-(4-acetyl-3-hydroxy-2-propylphenoxy)pentyloxy]-3,4-dihydro-2H-1-benzopyran-2-carboxylic acid to the 1–10 micron particle range by air attrition and place in an appropriate container. Add glyceryl trioleate at room temperature. Chill the Freon to −30° C. and then add it to mixture. Seal a precise appropriate volumetric valve into the container immediately after adding the Freon and place the container in an ultrasonic generator to disperse the racemic-6-acetyl-7-[5-(4-acetyl-3-hydroxy-2-propylphenoxy)pentyloxy-3,4-dihydro-2H-1-benzopyran-2-carboxylic acid in the Freon.

EXAMPLE 97

Aerosol Formulation (Sodium Salt Freon Suspension Aerosol)

| Ingredients | mg/100 μl | | |
|---|---|---|---|
| | 1 mg | 10 mg | 25 mg |
| Sodium Salt of racemic-6-acetyl-7-[5-(4-acetyl-3-hydroxy-2-propylphenoxy)-pentyloxy]-3,4-dihydro-2H—1-benzopyran-2-carboxylic acid (micronized) | 1 mg | 10 mg | 25 mg |
| Oleic Acid | 0.01 to 0.03 mg | 1.0 mg to 3.0 mg | 3.0 mg to 7.5 mg |
| Freon 114* 30 parts } To Make | 100 μl | 100 μl | 100 μl |
| Freon 12 70 parts | | | |

*Freon 11 can be substituted.

Procedure:

Micronize the sodium salt of racemic-6-acetyl-7-[5-(4-acetyl-3-hydroxy-2-propylphenoxy)pentyloxy]-3,4-dihydro-2H-1-benzopyran-2-carboxylic acid to the 1–10 micron particle range by air attrition and place in an appropriate container. Add glyceryl trioleate at room temperature. Chill the Freon to −30° C. and then add it to mixture. Seal a precise appropriate volumetric valve onto the container immediately after adding the Freon and place the container in an ultrasonic generator to disperse the sodium salt of racemic-6-acetyl-7-[5-(4-acetyl-3-hydroxy-2-propylphenoxy)pentyloxy]-3,4-dihydroxy-2H-1-benzopyran-2-carboxylic acid in the Freon.

EXAMPLE 98

Aerosol Formulation (Freon Solution Aerosol)

| Ingredients | mg/100 μl | | |
|---|---|---|---|
| | 1.0 mg | 10.0 mg | 25.0 mg |
| racemic-6-acetyl-7-[5-(4-acetyl-3-hydroxy-2-propylphenoxy)-pentyloxy]-3,4-dihydro-2H—1-benzopyran-2-carboxylic acid | 1.0 mg | 10.0 mg | 25.0 mg |
| Dimethylsulfoxide | 3.0 μl | 10.0 μl | 20.0 μl |
| Ethanol 99.9 | 6.0 μl | 6.0 μl | 6.0 μl |
| Methylene Chloride | 10 μl | 10 μl | 10 μl |
| Freon 12 To Make | 100 μl | 100 μl | 100 μl |

Procedure:

Dissolve racemic-6-acetyl-7-[5-(4-acetyl-3-hydroxy-2-propylphenoxy)pentyloxy]-3,4-dihydro-2H-1-benzopyran-2-carboxylic acid in dimethylsulfoxide at room temperature in an appropriate container. Add the ethanol and methylene chloride to the mixture. Then add the Freon which has been chilled to −30° C. Seal a precise appropriate volumetric valve onto the container immediately after adding the Freon.

EXAMPLE 99

Aerosol Formulation (Freon Solution Aerosol)

| Ingredients | |
|---|---|
| racemic-6-acetyl-7-[5-(4-acetyl-3-hydroxy-2-propylphenoxy)-pentyloxy]-3,4-dihydro-2H—1-benzopyran-2-carboxylic acid | 50.0 mg |
| Dimethylsulfoxide | 150 μl |
| Ethanol 99.9% | 0.3 ml |
| Methylene Chloride | 0.5 ml |
| Freon 12 | 4.2 ml |
| Total Volume | 5.0 ml |
| Concentration of Active Ingredient | 1 mg/0.1 ml |

Procedure: The same procedure as in Example 98 was employed in this Example.

EXAMPLE 100

Nebulization Formulation (Solution for Nebulization)

| Ingredients | mg/ml | | |
|---|---|---|---|
| | 25.0 mg | 50.0 mg | 100.0 mg |
| racemic-6-acetyl-7-[5-(4-acetyl-3-hydroxy-2-propylphenoxy)pentyloxy]-3,4-dihydro-2H—1-benzopyran-2-carboxylic acid | 25.0 mg | 50.0 mg | 100.0 mg |
| Phosphate Buffer Containing Sodium Hydroxide to pH 7.8 To Make | 1.0 ml | 1.0 ml | 1.0 ml |

Procedure:

Dissolve racemic-6-acetyl-7-[5-(4-acetyl-3-hydroxy-2-propylphenoxy)pentyloxy]-3,4-dihydro-2H-1-benzopyran-2-carboxylic acid into the phosphate buffer containing an equimolar amount of sodium hydroxide resulting in a solution having a pH of 7.8.

EXAMPLE 101

Capsule Formulation

| Ingredients | mg/capsule | | | |
|---|---|---|---|---|
| | 25 mg | 50 mg | 100 mg | 200 mg |
| racemic-6-acetyl-7-[5-(4-acetyl-3-hydroxy-2-propyl-phenoxy)pentyloxy]-3,4-di-hydro-2H—1-benzopyran-2-pentanoic acid | 25 | 50 | 100 | 200 |
| Lactose | 375 | 155 | 200 | 140 |
| Starch | 30 | 30 | 35 | 40 |
| Talc | 20 | 15 | 15 | 20 |
| Weight of capsule | 450 mg | 250 mg | 350 mg | 400 mg |

Procedure:
Mill racemic-6-acetyl-7-[5-(4-acetyl-3-hydroxy-2-propylphenoxy)pentyloxy-3,4-dihydro-2H-1-benzopyran-2-pentanoic acid, lactose and starch in a suitable mixer. Mill. Add talc and mix well. Encapsulate on suitable equipment.

EXAMPLE 102

Tablet Formulation (Wet granulation)

| Ingredients | mg/tablet | | | |
|---|---|---|---|---|
| | 25 mg | 50 mg | 100 mg | 200 mg |
| racemic-6-acetyl-7-[5-(4-acetyl-3-hydroxy-2-propyl-phenoxy)pentyloxy]-3,4-di-hydro-2H—1-benzopyran-2-pentanoic acid | 25 | 50 | 100 | 200 |
| Lactose | 280 | 153 | 187 | 171 |
| Modified Starch | 55 | 25 | 35 | 45 |
| Pregelatinized Starch | 35 | 20 | 25 | 30 |
| Distilled water q.s. | — | — | — | — |
| Magnesium Stearate | 5 | 2 | 3 | 4 |
| Weight of tablet | 400 mg | 250 mg | 350 mg | 450 mg |

Procedure:
Mix racemic-6-acetyl-7-[5-(4-acetyl-3-hydroxy-2-propylphenoxy)pentyloxy]-3,4-dihydro-2H-1-banzopyran-2-pentanoic acid, lactose, modified starch and pregelatinized starch in a suitable mixer. Granulate with sufficient distilled water to proper consistency. Mill. Dry in a suitable oven. Mill and mix with magnesium stearate for 3 minutes. Compress on a suitable press equipped with appropriated punches.

EXAMPLE 103

Tablet Formulation (Direction Compression)

| Ingredients | mg/tablet 25 mg |
|---|---|
| racemic-6-acetyl-7-[5-(4-acetyl-3-hydroxy-2-propyl-phenoxy)pentyloxy]-3,4-di-hydro-2H—1-benzopyran-2-pentanoic acid | 25 |
| Lactose | 181 |
| Avicel | 55 |
| Direct Compression Starch | 35 |
| Magnesium Stearate | 4 |
| Weight of tablet | 300 mg |

Procedure:
Mill racemic-6-acetyl-7-[5-(4-acetyl-3-hydroxy-2-propylphenoxy)pentyloxy]-3,4-dihydro-2H-1-benzopyran-2-pentanoic acid with an equal amount of lactose. Mix well. Mix with avicel and direct compression starch, and the remaining amount of lactose. Mix well. Add magnesium stearate and mix for 3 minutes. Compression on a suitable press equipped with appropriate punches.

We claim:

1. A compound of the formula

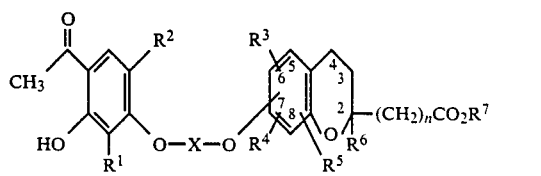

wherein $R_1$ is hydrogen or lower alkyl; $R^2$ is hydrogen or halogen, $R^3$, $R^4$ and $R^5$, independently, are hydrogen, alkanoyl, benzoyl or lower alkyl; $R^6$ and $R^7$, independently, are hydrogen or lower alkyl; X is alkylene of 3 to 7 carbon atoms; and n is as an integer of one to four provided one of $R^3$, $R^4$ or $R^5$ is alkanoyl or benzoyl and the other two, independently, are hydrogen or lower alkyl; or an enantiomer thereof, or, when $R^7$ is hydrogen, a salt thereof, with a pharmaceutically acceptable base.

2. A compound, in accordance with claim 1, wherein $R^1$ is lower alkyl, $R^2$ is hydrogen, $R^3$ is alkanoyl or benzoyl, and $R^4$, $R^5$, $R^6$ and $R^7$ are hydrogen.

3. A compound, in accordance with claim 2, wherein X is alkylene of 3 to 5 carbon atoms.

4. A compound, in accordance with claim 3, wherein $R^3$ is acetyl.

5. A compound, in accordance with claim 4, wherein $R^1$ is propyl.

6. A compound, in accordance with claim 1, racemic-6-acetyl-7-[3-(4-acetyl-3-hydroxy-2-propyl-phenoxy)propoxy3,4-dihydro]-2-methyl-8-n-propyl-2H-1-benzopyran-2-propanoic acid.

7. A compound, in accordance with claim 1, racemic-6-acetyl-7-[5-(4-acetyl-3-hydroxy-2-propyl-phenoxy)pentyloxy]-3,4-dihydro-2H-1-benzopyran-2-pentanoic acid.

8. A pharmaceutical composition having SRS-A antagonistic activity, comprising an effective amount of a compound of the formula

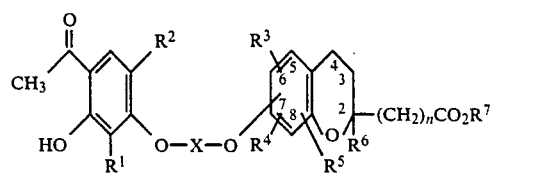

wherein $R_1$ is hydrogen or lower alkyl; $R^2$ is hydrogen or halogen; $R^3$, $R^4$ and $R^5$, independently, are hydrogen, alkanoyl, benzoyl or lower alkyl; $R^6$ and $R^7$, independently, are hydrogen or lower alkyl; X is alkylene of 3 to 7 carbon atoms; and n is an integer of one to four; provided that one of $R^3$, $R^4$ or $R^5$ is alkanoyl or benzoyl and the other two, independently, are hydrogen or lower alkyl; or an enantiomer thereof, or, when $R^7$ is hydrogen, a salt thereof, with a pharmaceutically acceptable base, and an inert carrier material.

9. A composition in accordance with claim 8, wherein the compound of formula I is racemic-6-acetyl-7-[3-(4-acetyl-3-hydroxy-2-propylphenoxy)propoxy]-3,4-dihydro-2-methyl-8-n-propyl-2H-1-benzopyran-2-propanoic acid.

10. A composition in accordance with claim 8, wherein the compound of formula I is racemic-6-acetyl-7-[5-(4-acetyl-hydroxy-2-propylphenoxy)pentyloxy]-3,4-dihydro-2H-1-benzopyran-2-pentanoic acid.

11. A method of treating allergic conditions requiring SRS-A antagonistic activity, which comprises administering an effective amount of a compound of the formula

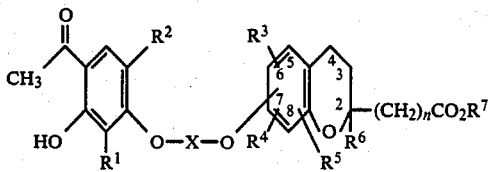

wherein $R_1$ is hydrogen or lower alkyl; $R^2$ is hydrogen or halogen; $R^3$, $R^4$ and $R^5$, independently, are hydrogen, alkanoyl, benzoyl or lower alkyl; $R^6$ and $R^7$, independently, are hydrogen or lower alkyl; X is alkylene of 3 to 7 carbon atoms; and n is an integer of one to four; provided that one of $R^3$, $R^4$ or $R^5$ is alkanoyl or benzoyl and the other two, independently, are hydrogen or lower alkyl; or an enantiomer thereof, or, when $R^7$ is hydrogen, a salt thereof, with a pharmaceutically acceptable base.

12. A method in accordance with claim 11, wherein the compound of formula I is racemic-6-acetyl-7-[3-(4-acetyl-3-hydroxy-2-propylphenoxy)propoxy]-3,4-dihydro-2-methyl-8-n-propyl-2H-1-benzopyran-2-propanoic acid.

13. A method in accordance with claim 11, wherein the compound of formula I is racemic-6-acetyl-7-[5-(4-acetyl-3-hydroxy-2-propylphenoxy]-3,4-dihydro-2H-1-benzopyran-2-pentanoic acid.

* * * * *

UNITED STATES PATENT AND TRADEMARK OFFICE
CERTIFICATE OF CORRECTION

PATENT NO. : 4,785,017

DATED : November 15, 1988

INVENTOR(S) : Noal Cohen and Guiseppe F. Weber

It is certified that error appears in the above-identified patent and that said Letters Patent is hereby corrected as shown below:

In claim 6, on the third line, "propoxy 3,4-dihydro]-2-methyl-8-n-" should be -- propoxy]-3,4-dihydro-2-methyl-8-n- --.

Signed and Sealed this

Second Day of January, 1990

*Attest:*

JEFFREY M. SAMUELS

*Attesting Officer*     *Acting Commissioner of Patents and Trademarks*